(12) United States Patent
Budigi et al.

(10) Patent No.: US 12,404,319 B2
(45) Date of Patent: Sep. 2, 2025

(54) METHODS AND COMPOSITIONS FOR TREATING YELLOW FEVER

(71) Applicant: WUXI BIOLOGICS IRELAND LIMITED, Dundalk (IE)

(72) Inventors: Yadunanda Kumar Budigi, Singapore (SG); Yok Hian Chionh, Singapore (SG); Debbie Ching Ping Lee, Singapore (SG); Megan Earley McBee, Singapore (SG)

(73) Assignee: WUXI BIOLOGICS IRELAND LIMITED, Dundalk (IE)

( * ) Notice: Subject to any disclaimer, the term of this patent is extended or adjusted under 35 U.S.C. 154(b) by 1078 days.

(21) Appl. No.: 17/066,299

(22) Filed: Oct. 8, 2020

(65) Prior Publication Data

US 2021/0139564 A1    May 13, 2021

Related U.S. Application Data

(63) Continuation of application No. PCT/US2019/027074, filed on Apr. 11, 2019.

(60) Provisional application No. 62/656,352, filed on Apr. 11, 2018.

(51) Int. Cl.
*C07K 16/10* (2006.01)
*A61K 39/00* (2006.01)
*A61P 31/14* (2006.01)

(52) U.S. Cl.
CPC .......... *C07K 16/1081* (2013.01); *A61P 31/14* (2018.01); *A61K 2039/505* (2013.01); *C07K 2317/41* (2013.01); *C07K 2317/76* (2013.01); *C07K 2317/92* (2013.01); *C07K 2317/94* (2013.01)

(58) Field of Classification Search
CPC ............ C07K 16/1081; C07K 2317/41; C07K 2317/76; C07K 2317/92; C07K 2317/94; A61P 31/14; A61K 2039/505
See application file for complete search history.

(56) References Cited

U.S. PATENT DOCUMENTS

2017/0355756 A1* 12/2017 Julien .................... C07K 16/18

FOREIGN PATENT DOCUMENTS

| CN | 101891806 A | 11/2010 | |
|---|---|---|---|
| CN | 107586335 A | 1/2018 | |
| JP | 2016-514675 A | 5/2016 | |
| WO | WO-2008068048 A2 * | 6/2008 | .............. A61P 31/10 |
| WO | WO 2014/144061 A2 | 9/2014 | |

(Continued)

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. (Year: 1995).*

(Continued)

*Primary Examiner* — Aurora M Fontainhas
*Assistant Examiner* — Selam Berhane
(74) *Attorney, Agent, or Firm* — James S. Keddie; Bozicevic, Field & Francis LLP

(57) ABSTRACT

The present disclosure is based, at least in part, on the discovery of antibodies that specifically bind YFV and/or neutralize the virus. Compositions and methods related to such antibodies or antigen-binding portions thereof are provided.

17 Claims, 2 Drawing Sheets

Specification includes a Sequence Listing.

(56) References Cited

FOREIGN PATENT DOCUMENTS

WO  WO 2017/189964 A2  11/2017

OTHER PUBLICATIONS

Edwards et al., The remarkable flexibility of the human antibody repertoire; isolation of over one thousand different antibodies to a single protein, BLyS. J Mol Biol. Nov. 14, 2003;334(1):103-18. (Year: 2003).*

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*

Kussie, Paul H., "A Single Engineered Amino Acid Substitution Changes Antibody Fine Specificity", 1994, Journal of Immunology 152(1): pp. 146-152. (Year: 1994).*

Deng et al., A broadly flavivirus cross-neutralizing monoclonal antibody that recognizes a novel epitope within the fusion loop of E protein. PLoS One. Jan. 11, 2011;6(1):e16059. doi: 10.1371/journal.pone.0016059.

Thibodeaux et al., A humanized IgG but not IgM antibody is effective in prophylaxis and therapy of yellow fever infection in an AG129/17D-204 peripheral challenge mouse model. Antiviral Res. Apr. 2012;94(1):1-8. doi: 10.1016/j.antiviral.2012.02.001. Epub Feb. 15, 2012.

International Search Report for Application No. PCT/US2019/027074, mailed Jul. 15, 2019.

International Preliminary Report on Patentability for Application No. PCT/US2019/027074, mailed Oct. 22, 2020.

Daffis et al., Antibody responses against wild-type yellow fever virus and the 17D vaccine strain: characterization with human monoclonal antibody fragments and neutralization escape variants. Virology. Jul. 5, 2005;337(2):262-72. doi: 10.1016/j.virol.2005.04.031.

Ryman et al., Mutation in a 17D-204 vaccine substrain-specific envelope protein epitope alters the pathogenesis of yellow fever virus in mice. Virology. Apr. 25, 1998;244(1):59-65. doi: 10.1006/viro.1998.9057.

PCT/US2019/027074, Jul. 15, 2019, International Search Report.
PCT/US2019/027074, Oct. 22, 2020, International Preliminary Report on Patentability.

* cited by examiner

METHODS AND COMPOSITIONS FOR TREATING YELLOW FEVER

RELATED APPLICATIONS

This application is a continuation of International Application No. PCT/US2019/027074, filed Apr. 11, 2019, which claims the benefit of priority under 35 U.S.C. § 119 of U.S. Provisional Application No. 62/656,352, filed Apr. 11, 2018, the entire contents of each of which are incorporated herein by reference.

BACKGROUND

Yellow fever is an acute viral haemorrhagic disease caused by the Yellow Fever Virus (YFV). In humans the primary vector for YFV transmission is the mosquito *Aedes aegypti*, which transmits several other viruses including Dengue and Zika Virus. YFV is endemic in tropical and subtropical areas of Africa and Central and South America. Infected individuals develop a wide range of symptoms from asymptomatic infection to acute viral hemorrhagic disease (10-15%), of which there is a 50% fatality rate. Since the 1930s, a live attenuated vaccine has been available on the market. However, a global shortage in supplies have hampered efforts to prevent and control YFV outbreaks. The most recent indication of this can be seen in Brazil, where the YFV has already infected over 700 people and claimed more than 200 lives since the outbreak began in 2017. Currently, there is no YFV therapy available to treat those who have not been vaccinated or in which the vaccine has not provided a protective effect. There is a need for YFV therapies.

SUMMARY OF THE INVENTION

The present disclosure is based, at least in part, on the discovery of antibodies that specifically bind YFV and/or neutralize the virus. For example, the antibodies, or antigen-binding portions thereof, can prevent YFV from infecting cells in some embodiments. In an embodiment, the antibodies, or antigen-binding portions thereof, of any one of the compositions or methods provided herein, specifically bind to engage the key epitope residues (N106, K93 and K104) that are the most solvent exposed and antibody-accessible on the E-protein. In an embodiment, the antibodies, or antigen-binding portions thereof, of any one of the compositions or methods provided herein, have energetically favorable paratope (CDR) interactions around these key epitope residues and/or are characterized by a threshold minimum binding energy.

Accordingly, one aspect of the present disclosure provides an antibody or antigen-binding portion thereof that specifically binds to the E-protein or an Envelope Protein Domain II (E-DII) epitope of Yellow Fever Virus. In an embodiment of any one of the compositions or methods provided herein, the E-protein or E-DII epitope comprises an asparagine at position 106, a lysine at position 93, and a lysine at position 104 of Yellow Fever Virus E-protein.

In an embodiment of any one of the methods or compositions provided, the antibody or antigen-binding portion comprises the three CDRs of a heavy chain variable region (VH). In an embodiment of any one of the methods or compositions provided, the three CDRs are those found in any one of the VH sequences set forth herein, such as in Table 1 (e.g., SEQ ID. NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, and 36). In an embodiment of any one of the methods or compositions provided, the antibody or antigen-binding portion thereof comprises the three CDRs of a light chain variable region (VL). In an embodiment of any one of the methods or compositions provided, the three CDRs are those found in any one of the VL sequences set forth herein, such as in Table 2 (SEQ ID. NOs: 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, and 73). In an embodiment of any one of the methods or compositions provided, the antibody or antigen-binding portion comprises the three CDRs of any one of the VH sequences set forth herein, such as in Table 1 (e.g., SEQ ID. NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, and 36) and the three CDRs of any one of the VL sequences set forth herein, such as in Table 2 (SEQ ID. NOs: 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, and 73). In an embodiment of any one of the methods or compositions provided, the antibody or antigen-binding portion thereof comprises the three CDRs of the VH sequence and the three CDRs of the VL sequence of any one of the specific combinations of VH sequences and VL sequences as set forth in Table 3. Thus, in an embodiment of any one of the methods or compositions provided herein, the antigen-binding portion thereof is an antigen-binding portion of such an antibody.

Provided herein in one aspect is a nucleic acid encoding the three CDRs of any one of the VH sequences provided herein, such as provided directly above, and/or the three CDRs of any one of the VL sequences provided herein, such as provided directly above.

In an embodiment of any one of the methods or compositions provided, the antibody or antigen-binding portion thereof comprises any one of the VH amino acid sequences provided herein, such as set forth in any one of SEQ ID. NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, and 36. In an embodiment of any one of the methods or compositions provided, the antibody or antigen-binding portion thereof comprises any one of the VL amino acid sequences provided herein, such as set forth in any one of SEQ ID. NOs: 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, and 73. In an embodiment of any one of the methods or compositions provided, the antibody or antigen-binding portion thereof comprises any one of the VH amino acid sequences provided herein, such as set forth in any one of SEQ ID. NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, and 36 and any one of the VL amino acid sequences provided herein, such as set forth in any one of SEQ ID. NOs: 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, and 73. In an embodiment of any one of the methods or compositions provided, the antibody or antigen-binding portion thereof comprises any one specific combination of the combinations of VH amino acid sequences and VL amino acid sequences provided herein, such as set forth in Table 3.

Provided herein in one aspect is a nucleic acid encoding any one of the VH sequences provided herein, such as provided directly above, and/or any one of the VL sequences provided herein, such as provided directly above.

In an embodiment of any one of the methods or compositions provided herein, the antibody or antigen-binding portion thereof comprises three CDRs that have at least 90%, 95%, 96%, 97%, 98% or 99% identity to the three CDRs of any one of the VH sequences set forth herein, such as in Table 1 (e.g., SEQ ID. NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, and 36). In an embodiment of any one of the methods or compositions provided, the antibody or antigen-binding portion thereof comprises three CDRs that have at least 90%, 95%, 96%, 97%, 98% or 99% identity to the three CDRs of any one of the VL sequences set forth herein, such as in Table 2 (SEQ ID. NOs: 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, and 73). In an embodiment of any one of the methods or compositions provided, the antibody or antigen-binding portion comprises three CDRs that have at least 90%, 95%, 96%, 97%, 98% or 99% identity to any one of the VH sequences set forth herein, such as in Table 1 (e.g., SEQ ID. NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, and 36) and three CDRs that have at least 90%, 95%, 96%, 97%, 98% or 99% identity to any one of the VL sequences set forth herein, such as in Table 2 (SEQ ID. NOs: 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, and 73). In an embodiment of any one of the methods or compositions provided, the antibody or antigen-binding portion thereof comprises three CDRs that have at least 90%, 95%, 96%, 97%, 98% or 99% identity to the VH sequence and three CDRs that have at least 90%, 95%, 96%, 97%, 98% or 99% identity to the VL sequence of any one of the specific combinations of VH sequences and VL sequences provided herein, such as set forth in Table 3. Thus, in an embodiment of any one of the methods or compositions provided herein, the antigen-binding portion thereof is an antigen-binding portion of such an antibody.

Provided herein in one aspect is a nucleic acid encoding the three CDRs of any one of the VH sequences provided herein, such as provided directly above, and/or the three CDRs of any one of the VL sequences provided herein, such as provided directly above.

In an embodiment of any one of the methods or compositions provided, the antibody or antigen-binding portion thereof comprises a VH amino acid sequence that has at least 85%, 90%, 95%, 96%, 97%, 98% or 99% identity to any one of the VH amino acid sequences provided herein, such as set forth in any one of SEQ ID. NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, and 36. In an embodiment of any one of the methods or compositions provided, the antibody or antigen-binding portion thereof comprises a VL sequence that has at least 85%, 90%, 95%, 96%, 97%, 98% or 99% identity to any one of the VL amino acid sequences provided herein, such as set forth in any one of SEQ ID. NOs: 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, and 73. In an embodiment of any one of the methods or compositions provided, the antibody or antigen-binding portion thereof comprises a VH amino acid sequences that has at least 85%, 90%, 95%, 96%, 97%, 98% or 99% identity to any one of the VH amino acid sequences provided herein, such as set forth in any one of SEQ ID. NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, and 36 and a VL sequence that has at least 85%, 90%, 95%, 96%, 97%, 98% or 99% identity to any one of the VL amino acid sequences provided herein, such as set forth in any one of SEQ ID. NOs: 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, and 73. In an embodiment of any one of the methods or compositions provided, the antibody or antigen-binding portion thereof comprises a VH sequence and a VL sequence that each independently have at least 85%, 90%, 95%, 96%, 97%, 98% or 99% identity to the VH and VL sequences of any one specific combination of the combinations of VH amino acid sequences and VL amino acid sequences provided herein, such as set forth in Table 3.

Provided herein in one aspect is a nucleic acid encoding the VH sequence as provided directly above and/or the VL sequences as provided directly above.

In an embodiment of any one of the methods or compositions provided herein, the antigen-binding portion thereof is an antigen-binding portion of any one of the antibodies provided herein.

Any one of the antibodies described herein can be a full-length antibody. The antibody or antigen-binding portion thereof can be human, humanized, or chimeric in an embodiment of any one of the methods or compositions provided herein. The antibody or antigen-binding portion thereof can be a single-chain antibody in an embodiment of any one of the methods or compositions provided herein. Any of the antibodies described herein can be either monoclonal or polyclonal. These two terms do not limit the source of an antibody or the manner in which it is made. The antibody or antigen-binding portion thereof can be a monoclonal antibody or antigen-binding portion thereof in an embodiment of any one of the methods or compositions provided herein. Further, the antigen-binding portion thereof can be an scFv, a F(ab')2 fragment, a dAb fragment, a Fab fragment, a Fab' fragment, an Fv, or a disulfide-linked Fv fragment in an embodiment of any one of the methods or compositions provided herein. The antibody or antigen-binding portion thereof may be a single domain antibody, a diabody, a multispecific antibody, a bispecific antibody, or a dual-specific antibody. The antibody or antigen-binding portions thereof may be an isolated antibody or antigen-binding portion thereof in an embodiment of any one of the methods or compositions provided herein.

Further disclosed are methods of treating Yellow Fever, or a disease or condition associated with Yellow Fever Virus, by administering a therapeutically effective amount of one or more antibodies or antigen-binding portions thereof that specifically bind YFV, to a subject in need of such treatment. In an embodiment of any one of the methods provided herein, the subject has not been vaccinated for the YFV or in which a YFV vaccination did not provide an adequate protective effect. In an embodiments of any one of the method or compositions provided herein, the antibodies or antigen-binding portions thereof are any one or more of the antibodies or antigen-binding portions thereof described herein. In an embodiment of any one of the methods or compositions provided herein, the antibody or antigen-binding portion thereof specifically binds to the E-protein or an E-DII epitope of YFV. In an embodiments of any one of the methods or composition provided herein, the antibody or antigen-binding portion thereof specifically binds to residues 93, 104, and 106 of the E-protein or E-DII epitope of Yellow Fever Virus E-protein. In an embodiment of any one of the methods or compositions provided herein, the amount of the antibody or antigen-binding portion thereof is effective in reducing one or more symptoms of Yellow Fever in the subject. Any one of the anti-YFV antibodies or antigen-binding portions thereof may be administered systemically, e.g., via an enteral route or via a parenteral route, in any one of the methods provided herein.

The subject to be treated in any one of the methods described herein can be a patient (e.g., a human patient) who has or is suspected of having Yellow Fever, or a disease or condition associated with Yellow Fever Virus. In an embodiment of any one of the methods provided herein, the subject is a human patient who has or is suspected of having acute viral hemorrhagic disease.

Also provided herein in some aspects are (a) pharmaceutical compositions for use in treating Yellow Fever or a disease or condition associated with Yellow Fever Virus (e.g., acute viral hemorrhagic disease) in a subject, the pharmaceutical composition comprising any one or more of the antibodies or antigen-binding portions thereof described herein and a pharmaceutically acceptable carrier; and (b) uses of the just-described antibodies or antigen-binding portions thereof in medicaments and/or in the manufacturing of a medicament for treatment of Yellow Fever or a disease or condition associated with Yellow Fever Virus in a subject.

Also provided herein in some aspects are methods for producing the antibodies or antigen-binding portions thereof, nucleic acids encoding any one of the antibodies or antigen-binding portions thereof, vectors that can comprise any one or more of the nucleic acids provided herein, and related host cells.

In one aspect the method for producing the antibodies or antigen-binding portions thereof is any one of the methods described herein. In one embodiment, the method comprises considering the distinct domain proximal structural regions present on the viral assembly (e.g. inter-chain interfaces near the icosahedral axes of symmetry) and selecting promising Fv scaffolds. Conventional epitope prediction methods use domain structures to predict epitope surface regions embedded within the domain region. However, neutralizing flaviviral antibodies can recognize quaternary epitope surfaces (spanning two or more E protein chains). Thus, traditional methods do not incorporate valuable information.

BRIEF DESCRIPTION OF DRAWINGS

FIG. 2A shows the survival curve of YF-17D infected AG129 mice treated with mAb at a dose of 10 mg/kg as prophylaxis (−1) or as Therapy (+1 and +1, +4). FIG. 2B shows blood viral titers of yellow fever virus in treated animals compared with control groups at Days 4 and 6 post infection. The administration of mAb resulted in complete protection compared to control groups (FIG. 2A). Administration of mAb also led to greater than 2 Log 10 reduction in viremia at days 4 and 6 post infection (FIG. 2B).

DETAILED DESCRIPTION

Figure 1:
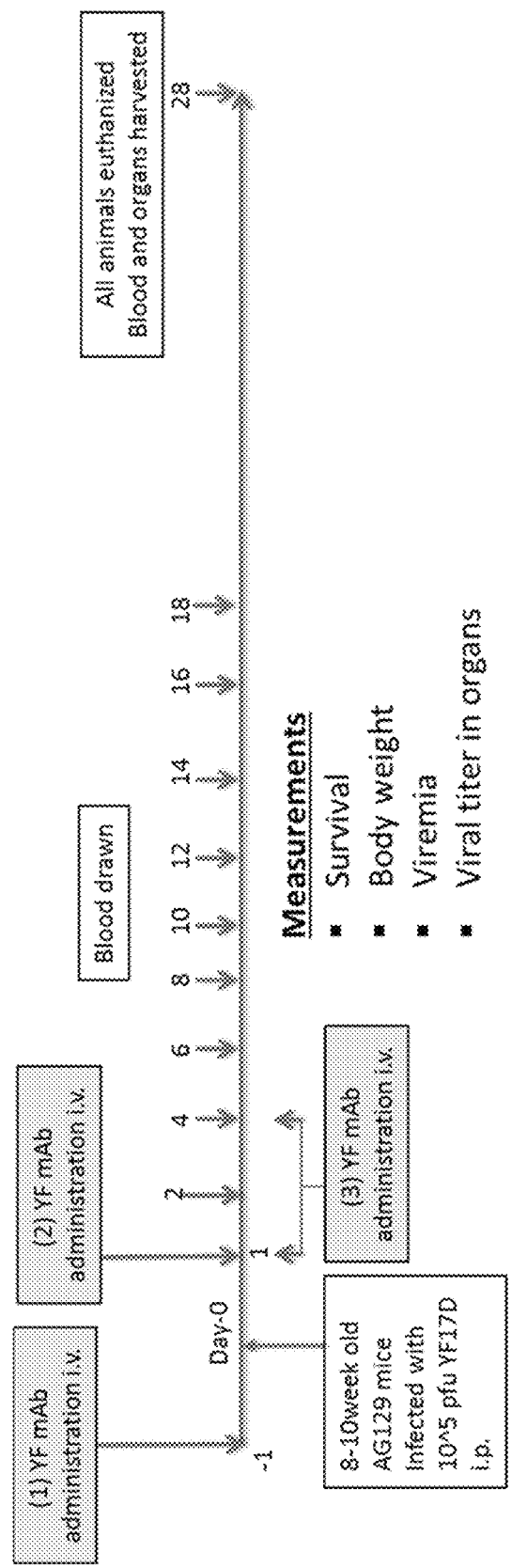
FIG. 1 shows an example an in vivo study design of efficacy of engineered mAbs against YF-17D-204 in a mouse model of infection. Efficacy of designed mAbs was tested in a lethal model of Yellow fever infection in AG129 mice. Protective efficacy of mAbs was tested in prophylaxis or as therapy.

The following description is merely intended to illustrate various embodiments of the invention. As such, specific embodiments discussed herein are not to be construed as limitations to the scope of the invention. It will be apparent to one skilled in the art that various changes or equivalents may be made without departing from the scope of the invention.

Various aspects of the disclosure relate to antibodies, antigen-binding portions thereof, and pharmaceutical compositions thereof, as well as nucleic acids, recombinant expression vectors and host cells for making such antibodies and fragments. Provided herein are antibodies and/or antigen-binding portions thereof that specifically bind Yellow Fever Virus (YFV) and/or neutralize the virus. In some embodiments, the antibody or antigen-binding portion thereof binds to an E-DII epitope of the Yellow Fever Virus and prevents the virus from infecting cells. In some embodiments, the antibody or antigen-binding portion thereof binds to an E-DII epitope comprising an asparagine at position 106, a lysine at position 93 and/or a lysine at position 104 of Yellow Fever Virus E-protein. The antibodies and antigen-binding portions, as provided herein, in some embodiments, are used to treat or prevent Yellow Fever Virus infection in a subject.

An antibody (interchangeably used in plural form), as used herein, broadly refers to an immunoglobulin (Ig) molecule or any functional mutant, variant, or derivation thereof. It is desired that functional mutants, variants, and derivations thereof, as well as antigen-binding portions, retain the essential epitope binding features of an Ig molecule.

Antibodies are capable of specific binding to a target through at least one antigen recognition site, located in the variable region of the immunoglobulin molecule. Generally, an intact or full-length antibody comprises two heavy chains and two light chains. Each heavy chain contains a heavy chain variable region (VH) and a first, second and third constant regions ($C_H1$, $C_H2$ and $C_H3$). Each light chain contains a light chain variable region (VL) and a constant region (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. A full-length antibody can be an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The term "antigen-binding portion refer to a portion or region of an intact or full-length antibody molecule that can bind specifically to a target. Preferably, antigen-binding portions provided herein retain the ability to specifically bind to YFV. An antigen-binding portion may comprise the heavy chain variable region (VH), the light chain variable region (VL), or both. Each of the VH and VL typically contains three complementarity determining regions CDR1, CDR2, and CDR3.

Examples of antigen-binding portions include, but are not limited to: (1) an Fab fragment, which can be a monovalent fragment having a VL-CL chain and a VH-CH chain; (2) an F(ab')2 fragment, which can be a bivalent fragment having two Fab fragments linked by a disulfide bridge at the hinge region, i.e. a dimer of Fab; (3) an Fv fragment having the VL and VH domains of a single arm of an antibody; (4) a single chain Fv (scFv), which can be a single polypeptide chain composed of a VH domain and a VL domain through a peptide linker; (5) a (scFv)₂, which can comprise two VH domains linked by a peptide linker and two VL domains, which are associated with the two VH domains via disulfide bridges; 6) a Fd fragment consisting of the VH and CHI domains; (7) a dAb fragment, which comprises a single variable domain; and (8) an isolated complementarity determining region (CDR).

Furthermore, although the two domains of the Fv fragment, VL and VH, can be coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2: 1121-1123). Diabodies are also encompassed within the term "antigen-binding portion".

The term "human antibody" refers to antibodies having variable and constant regions corresponding substantially to, or derived from, antibodies obtained from human subjects, e.g., encoded by human germline immunoglobulin sequences or variants thereof. The human antibodies described herein may include one or more amino acid residues not encoded by human germline immunoglobulin sequences (e.g., mutations introduced by random or site-specific mutagenesis in vitro or by somatic mutation in vivo). Such mutations may present in one or more of the CDRs, particularly CDR3, or in one or more of the framework regions. In some embodiments, the human antibodies may have at least one, two, three, four, five, or more positions replaced with an amino acid residue that is not encoded by the human germline immunoglobulin sequence. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29: 128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or antibodies prepared, expressed, created or isolated by any other means that involves splicing of human immunoglobulin gene sequences to other DNA sequences. Such recombinant human antibodies have variable and constant regions as defined above. In certain embodiments, however, such recombinant human antibodies may be subjected to in vitro mutagenesis (or, when an animal transgenic for human Ig sequences is used, in vivo somatic mutagenesis) and thus the amino acid sequences of the VH and VL regions of the recombinant antibodies may be sequences that, while derived from and related to human germline VH and VL sequences, may not naturally exist within the human antibody germline repertoire in vivo.

Some embodiments of the disclosure provide fully human antibodies capable of binding the E-DII epitope of Yellow Fever Virus. In some embodiments, the E-DII epitope comprises an asparagine at position 106, a lysine at position 93, and a lysine at position 104 of Yellow Fever Virus E-protein.

The protein sequences for the various VH and VL regions are displayed in Table 1 and Table 2 respectively.

TABLE 1

Protein sequence for variable heavy chains

```
>VH.01; SEQ ID NO: 1
EVKLVESGGGLVKPGGSLKLSCAASGFTFTNYAMSWVRQTPEKRLEWVASISSGHTPYYPDSVKGRFTISRDNA
RNILFLQMSSLRSEDTAMYYCARGDYYGSVYSAMDYWGQGTSVTVSS

>VH.11; SEQ ID NO: 2
EVQLVESGGGLVQPGRSLRLSCAASGFTFTNYAMSWVRQAPGKGLEWVSSISSGHTPYYPDSVKGRFTISRDNA
KKSLYLQMNSLRAEDTALYYCARGDYYGSVYSAMDYWGQGTTVTVSS

>VH.21; SEQ ID NO: 3
EVQLVESGGGLVQPGRSLRLSCAASGFTFTDYYMSWVRQAPGKGLEWVSSISSGHTPYYPDSVKDRFTISRDNA
KKSLYLQMNSLRAEDTALYYCARGDYYGTVYSAMDYWGQGTTVTVSS

>VH.31; SEQ ID NO: 4
EVQLVESGGGLVQPGRSLRLSCAASGYAFTNYAMSWVRQAPGKGLEWVSSISSGHTPYYPDTVKGRFTISRDN
AKKSLYLQMNSLRAEDTALYYCARGDYYGSSYSAMDYWGQGTTVTVSS

>VH.3.11; SEQ ID NO: 5
EVQLVESGGGLVQPGRSLRLSCAASGYAFTNYGVNWVRQAPGKGLEWVSSISSGGSTYYPDSVKGRFTISRDNA
KKSLYLQMNSLRAEDTALYYCARHDYYGSSY-AMDYWGQGTTVTVSS
```

TABLE 1-continued

Protein sequence for variable heavy chains

>VH.3.21; SEQ ID NO: 6
EVQLVESGGGLVQPGRSLRLSCAASGYAFTNYGVNWVRQAPGKGLEWVSSISSGGSTYYPDSVKGRFTISRDNA
KKSLYLQMNSLRAEDTALYYCARSHYYGSSYDAMDYWGQGTTVTVSS

>VH.41; SEQ ID NO: 7
EVQLVESGAEVKKPGSSVKVSCKASGFTFTNYAMSWVRQAPGQGPEWMGSISSGHTPYYPDSVKGGRVTITA
DDFAGTVYMELSSLRSEDTAMYYCRGDYYGSVYSAMDYWGKGTTVTVSS

>VH.51; SEQ ID NO: 8
EVQLVESGAEVKKPGSSVKVSCKASGFTFTNYAMSWVRQAPGQGPEWMGSISSGHTPYYPDSVKGRVTITAD
DFAGTVYMELSSLRSEDTAMYYCARGDYYGSVYSAMDYWGKGTTVTVSS

>VH.61; SEQ ID NO: 9
QVQLVQSGAEVKKPGASVKVSCKAGFTFTNYAMSWVRQAPEQGLEWMGSISSGHTPYYPDSVKGRVTMTAD
TSTNTAYMELRSLRSDDTAVYYCARGDYYGSVYSAMDYWGQGTLVTVSS

>VH.71; SEQ ID NO: 10
EVQLVESGGGLVQPGGSLRLSCSASGFTFTNYAMSWVRQAPGKGLEYVSSISSGHTPYYPDSVKGRFTISRDNSK
NTLYFEMNSLRPEDTAVYYCVRGDYYGSVYSAMDYWGQGTTVTVSS

>VH.1; SEQ ID NO: 11
ASVLSEVQLQQSGPELVKPGASVKLSCKTSENTFTEYTMHWVKQSHGKSLEWIGGIDPNNGGTNYNQKFKGK
ATLTVDKSSNTAYMELRSLTSEDSAVYYCGRRDYYALDYWGQGTSVTVAS

>VH.2; SEQ ID NO: 12
QVQLQQPGAELVKPGASVKLSCKASGYTFTSYWMHWVKLRPGQGFEWIGDINPNNGGPSYNEKFKRKATLTV
DTSSSTAYMQLSSLTSEDSAVYYCTIDDGYRFGYWGQGTLVTVSA

>VH.3; SEQ ID NO: 13
QVQLQQSGSELMKPGASVQISCKATGYTFSDYWIEWVKQRPGHGLEWIGDILCGTGRTRYNEKLKAMATFTA
DTSSNTAFMQLSSLTSEDSAVYYCARSASYGDYADYWGHGTTLTVSS

>VH.4; SEQ ID NO: 14
AQLQQSGTGLARPGASVKLSCKASGYTFTSYGISWVTQRAGQGLEWIGVIYPRSGNTYYNEKFRGKATLTADKS
SSSAYMELRGLTAEDSAVYFCARENYGSVYWGQGTTLTVSS

>VH.5; SEQ ID NO: 15
EVQLQQSGAELVKPGASVKLSCTASGFNIKDTYMHWVKQRPEQGLEWIGRIDPANGYSKYDPKFQGKATITAD
TSSNAAYLQLSSLTSEDTAVYFCARDYEGFAYWGQGTLVTVSS

>VH.6; SEQ ID NO: 16
EVQLVESGGGVVQPGRSLRLSCAASGFSFSSYGMHWVRQAPGKGLEWVAVIWYDGSKTYYGDSVKGRFTISK
DNSKKMVNLQMDSLGVEDTAFYYCARGIAGGWAFWGIDLWGQGTLVTVSS

>VH.7; SEQ ID NO: 17
EVQLQQSGAELVKPGASVKLSCTASGFNIKDTYMHWVKQRPEQGLEWIGRIDPANGYSKYDPKFQGKATITAD
TSSNAAYLQLSSLTSEDTAVYFCARDYEGFAYWGQGTLVTVSS

>VH.8; SEQ ID NO: 18
EVQLVQSGAEVRKPGASTKVSCKASGYTFTHYYMHWVRQAPGQGLEWMGIINPSGGSTTYAQKLQGRVTMT
RDTSTSTVYMELSSLRSEDTAVYYCARDWGSNYVWGSYPKYWGQGTLVTVSS

>VH.9; SEQ ID NO: 19
EVQLVESGGGLVQPGRSLRLSCAASGFTFNDYAMHWVRQAPGKGLEWVSTISWNSGSIGYADSVKGRFTISR
DNAKKSLYLQMNSLRAEDTALYYCAKDIQYGNYYYGMDVWGQGTTVTVSS

>VH.10; SEQ ID NO: 20
DVQLVEPGAELVQPGASVKMSCKASGYTFSSYWINWEKQRPGKGLEWIGNIYPGSGTVNYDDKFKSKATLTID
TSSNTAYMQLSSLTSEDSAVYYCTRGGSHAMDYWGQGTSVTVSS

>VH.11; SEQ ID NO: 21
EVQLVESGGGLVRPGGSLRLSCAASGFSYSNHWMHWVRQAPGKGLVWVSRINSDGSTRNYADFVKGRFTISR
DNAENTLYLEMNSLTADDTAVYYCVRDGVRFYYDSTGYYPDSFFKYGMDVWGQGTTVTVSS

>VH.12; SEQ ID NO: 22
EVQLVESGGGLVRPGGSLRLSCAASGFSYSNHWMHWVRQAPGKGLVWVSRINSDGSTRNYADFVKGRFTISR
DNAENTLYLEMNSLTADDTAVYYCVRDGVRFYYDSTGYYPDSFFKYGMDVWGQGTTVTVSS

>VH.13; SEQ ID NO: 23
EVKLVESGGGLVLPGGSLRLSCATSGFTFTDYYMTWVRQPPGKALEWLGFIGNKANDYTTEYSASVKGRFTISR
DDSQSILYLQMSTLRAEDRATYYCATVYGNYPYFDVWGAGTTVAVSS

>VH.14; SEQ ID NO: 24
EVQLVESGAEVKKPGSSVKVSCKASGGTFNNYAISWVRQAPGQGLEWMGGIIPIFGGANYAQKFQGRVTITAD
RSTSTVYMELSGLRSEDTAVYYCARRPQSIFDWNFDLWGRGTLVTVSSAGTKGPS

TABLE 1-continued

Protein sequence for variable heavy chains

>VH.15; SEQ ID NO: 25
EVQLVESGGGLVQPGGSLKLSCAASGFTFSSHWMHWVRQAPGKGLVWVSRTNSDGSSTSYADSVKGRFMIS
RDNSKNTVYLHMNGLRAEDTAVYFCARDGVRYYYDSTGYYPDNFFQYGLDVWGQGTTVTVSSA

>VH.16; SEQ ID NO: 26
EVQLQQSGPELVKPGASVKISCKASGYTFTDYNMHWVKQSHGKSLEWVGYTYPYNGGIGYNQKFKSKATLTLD
NSSRTAYMELRSLTSEDSAVYYCVRRGYRYDGAHFDYWGQGTTLTVSS

>VH.17; SEQ ID NO: 27
DVQLVESGGGLVQPGGSRKLSCAASGFTFSSFGMHWVRQAPEKGLEWVAYISSGSSTLHYADTVKGRFTISRD
NPKNTLFLQMTSLRSEDTAMYYCARWGNYPHYAMDYWGQGTSVTVSS

>VH.18; SEQ ID NO: 28
QVQLVQSGAEVKKPGASVKVSCKAGFNIKDVYMSWVRQAPEQGLEWMGRIDPENGDTKYDPKLQGRVTMT
ADTSTNTAYMELRSLRSDDTAVYYCARGWEGFAYWGQGTLVTVSS

>VH.19; SEQ ID NO: 29
EVQLVESGGGLVQPGGSLRLSCSASGFTFSTYSMHWVRQAPGKGLEYVSAITGEGDSAFYADSVKGRFTISRDN
SKNTLYFEMNSLRPEDTAVYYCVGGYSNFYYYTMDVWGQGTTVTVSSG

>VH.20; SEQ ID NO: 30
EVQLVESGGGLVRPGGSLRLSCAASGFSYSNHWMHWVRQAPGKGLVWVSRINSDGSTRNYADFVKGRFTISR
DNAENTLYLEMNSLTADDTAVYYCVRDGVRFYYDSTGYYPDSFFKYGMDVWGQGTTVTVSS

>VH.21; SEQ ID NO: 31
DVQLVESGGGLVQPGGSRKLSCAASGFTFSSFGMHWVRQAPEKGLEWVAYISSGSSTLHYADTVKGRFTISRD
NPKNTLFLQMTSLRSEDTAMYYCARWGNYPHYAMDYWGQGTSVTVSS

>VH.22; SEQ ID NO: 32
QVQLQQPGAELVKPGASVKMSCKASGYTFTSYNMHWVKQTPGRGLEWIGAIYPGNGDTSYNQKFKGKATLT
ADKSSSTAYMQLSSLTSEDSAVYYCARSTYYGGDWYFNVWGAGTTVTVSA

VH.23; SEQ ID NO: 33
QVQLVQSGAEVKKPGSSVKVSCKASGYAFSYSWINWVRQAPGQGLEWMGRIFPGDGDTDYNGKFKGRVTIT
ADKSTSTAYMELSSLRSEDTAVYYCARNVFDGYWLVYWGQGTLVTVSS

>VH.24; SEQ ID NO: 34
EVQLVESGAEVKKPGSSVKVSCKASGGPFRSYAISWVRQAPGQGPEWMGGIIPIFGTTKYAPKFQGRVTITADD
FAGTVYMELSSLRSEDTAMYYCAKHMGYQVRETMDVWGKGTTVTVSS

>VH.25; SEQ ID NO: 35
EVQLLESGGGLVQPGGSLRLSCAASGFTFSSYIMMWVRQAPGKGLEWVSSIYPSGGITFYADTVKGRFTISRDN
SKNTLYLQMNSLRAEDTAVYYCARIKLGTVTTVDYWGQGTLVTVSS

>VH.26; SEQ ID NO: 36
QVTLRESGPALVKPTQTLTLTCTFSGFSLSTAGMSVGWIRQPPGKALEWLADIWWDDKKHYNPSLKDRLTISKD
TSKNQVVLKVTNMDPADTATYYCARDMIFNFYFDVWGQGTTVTVSS

TABLE 2

Protein sequence for variable light chains

>VL.0; SEQ ID NO: 37
DIRMTQSPSSMYASLGERVTVTCKASQDINSYLSWLQQKPGKSPKTLIYRANRLFDGVPSRFSGSGSGQDYSLTIS
SLEYEDMGIFYCLQYDEFPFTFGSGTKLEIK

>VL.111; SEQ ID NO: 38
DIRMTQSPSSLSASVGDRVTITCKASQDINSYLSWLQQKPGKSPKTLIYRANRLFDGVPSRFSGSGSGTDFTLTISS
LQPEDFAIYYCLQYDEFPFTFGSGTKVEIK

>VL.1.11; SEQ ID NO: 39
DIRMTQSPSSLSASVGDRVTITCKASQDINSYLNWLQQKPGKSPKTLIYRVNRLVDGVPSRFSGSGSGTDFTLTIS
SLQPEDFAIYYCLQYDEFPYTFGSGTKVEIK

>VL.1.21; SEQ ID NO: 40
DIRMTQSPSSLSASVGDRVTITCKASQDIKSYLSWLQQKPGKSPKTLIYRVNRLVDGVPSRFSGSGSGTDFTLTISS
LQPEDFAIYYCLQYDEFPYTFGSGTKVEIK

>VL.1.31; SEQ ID NO: 41
DIRMTQSPSSLSASVGDRVTITCKASQDINSYLNWLQQKPGKSPKTLIYRVNRLVDGVPSRFSGSGSGTDFTLTIS
SLQPEDFAIYYCLHYDEFPYTFGSGTKVEIK

>VL.1.41; SEQ ID NO: 42
DIRMTQSPSSLSASVGDRVTITCKASQDIKSYLSWLQQKPGKSPKTLIYRVNRLVDGVPSRFSGSGSGTDFTLTISS
LQPEDFAIYYCLHYDEFPYTFGSGTKVEIK

TABLE 2-continued

Protein sequence for variable light chains

>VL.211; SEQ ID NO: 43
DIRMTQSPSSLSASVGDRVTITCRASQDINSYLSWLQQKPGKSPKTLIYRANRLMIGVPSRFSGSGSGTDFTLTISS
LQPEDFAIYYCLQYDDFPLTFGSGTKVEIK

>VL.311; SEQ ID NO: 44
DIRMTQSPSSLSASVGDRVTITCKASQDINSFLTWLQQKPGKSPKTLIYRANRVFDGVPSRFSGSGSGTDFTLTISS
LQPEDFAIYYCLQYDDFPLTFGSGTKVEIK

>VL.411; SEQ ID NO: 45
QSVLTQPPSVSAAPGQKVTISCKASQDINSYLSWYQQLPGTAPKLLIYRANRLFDGIPDRFSGSKSGTSATLGITGL
QTGDEANYYCLQYDEFPFTFGGGTKLTVL

>VL.511; SEQ ID NO: 46
DIVMTQSPASLAVSLGQRATISCKASQDINSYLSWYQQKPGQPPKLLIYRANRLFDGVPDRFSGSGSGTDFTLTIS
SLQAEDVAVYYCLQYDEFPFTFGQGTKLEIKR

>VL.611; SEQ ID NO: 47
EIVLTQSPATLSLSPGERATLSCKASQDINSYLSWYQHKPGQAPRLLIYRANRLFDGVPARFSGSRSGTDFTLTISTL
EPEDFAVYYCQLQYDEFPFTFGQGTKVEIK

>VL.1; SEQ ID NO: 48
DIVMTQSQKFMSTSVGDRVSITCKASQHVGSAVAWYQQKPGQSPTLLIHSASNRYTGVPDRFTGSGSGTDFTLT
ISNIQSEDLADYFCQQYNSYPTFGGGTKLEIK

>VL.2; SEQ ID NO: 49
DIQMTQSPASLSASVGETVTITCRASGNIHNYLAWYQQKQGKSPQLLVYNAKTLADGVPSRFSASGSGTQYSLKI
NSLQPEDFGSYYCQHFWSTPRTFGGGTKLEIKR

>VL.3; SEQ ID NO: 50
DIVMTQSHKFMSTSVGDRVSITCKASQDVSTAVAWYQQKPGQSPKLLISWASTRHTGVPDRFTGSGSGTDYTLT
ISSVQAEDLALYYCQQHYTTPLTFGAGTKLELK

>VL.4; SEQ ID NO: 51
DIVMTQSQKFMSTSVGDRVSITCKASQNVGTAVAWYQQKPGQSPKLLIYSASNRYTGVPDRFTGSGSGTDFTLT
ISNMQSEDLADYFCQQFSSYPYTFGGGTKLEIK

>VL.5; SEQ ID NO: 52
DIVLTQSPASLAVSLGQRATISCRASESVVRYGNSFMHWYQQKPGQPPKLLIYRASSLESGIPTRFSGSGSRTDFTL
TINPVEADDVATYYCQQTNVDPWAFGGGTKLEIK

>VL.6; SEQ ID NO: 53
DVVMTQSPGTLSLSPGERATLSCRASQNVYSYLGWYQHKPGRSPRLLIFGVTSRATGVPDRFSGSGSGTDFTLTIS
RLEPEDFAVYYCQQYAGSAYTFGQGTKVEIKR

>VL.7; SEQ ID NO: 54
DIVLTQSPASLAVSLGQRATISCRASESVVRYGNSFMHWYQQKPGQPPKLLIYRASSLESGIPTRFSGSGSRTDFTL
TINPVEADDVATYYCQQTNVDPWAFGGGTKLEIK

>VL.8; SEQ ID NO: 55
QSVLTQPSSVSGTPGQRVTISCSGSSSNIGSNTVNWYQQLPGTAPKLLIYGNNQRPSGVPDRFSGSKSGTSASLAI
SGLQSEDEADYYCAAWDDSLNGPVFGGGTKLTVLG

>VL.9; SEQ ID NO: 56
DIQMTQSPSSLSASVGDRVTITCRTSQSISSYLNWYQQKPGKAPKLLIYAASSLQSGVPSRFSGSGSGTDFTLTISSL
QPEDFATYYCQQSYSTPRTFGQGTKVEIK

>VL.10; SEQ ID NO: 57
DIVMTQSQKFMSTSVGDRVSITCKASQNVRTSVAWYQQKPGQSPKALIYLASNRHTGVPDRFTGSGSGTDFTLT
ISNVQSEDLADYFCLQHWTYPYTFGGGTKLEIK

>VL.11; SEQ ID NO: 58
GASQSVLTQPVSVSGSPGQSITISCTGTSSNADTYNLVSWYQQRPGKAPKLMIYEGTKRPSGVSNRFSASKSATA
ASLTISGLQPEDEADYYCCSYATSRTLVFGGGTKLTVV

>VL.12; SEQ ID NO: 59
GASQSVLTQPVSVSGSPGQSITISCTGTSSNADTYNLVSWYQQRPGKAPKLMIYEGTKRPSGVSNRFSASKSATA
ASLTISGLQPEDEADYYCCSYATSRTLVFGGGTKLTVVAA

>VL.13; SEQ ID NO: 60
QIVLTQSPAIMSASPGEKVTMTCSASSSVSYMHWYQQKSGTSPKIWIYESSKLASGVPVRFSGSGSGTSYSLTISS
MEAEDVATYYCQQWSSHPHPLTFGAGTKLELK

>VL.14; SEQ ID NO: 61
QSVLTQPPSASGTPGQRVTISCSGSSSNVGSNYVYWYQQLPGTAPKLLIYRNNRRPSGVPDRFSGSKSGTSASLAI
SGLRSEDEADYYCATWDDSLSGLVFGGGTKLTVLGQPKA

TABLE 2-continued

Protein sequence for variable light chains

```
>VL.15; SEQ ID NO: 62
RSQSALTQPASVSGSPGQSITISCTGISSDVETYNLVSWYEQHPGKAPKLIIYEASKRPSGVSNRFSGSKSGNTASLA
ISGLQAEDEADYYCCSYAGGKSLVFGGGTRLTVLGQP

>VL.16; SEQ ID NO: 63
DIKMTQSPSSMYASLGERVTITCKASQGINSDLSWFQQKPGKSPKTLIYRANRLVDGVPSRFSGSGSGQDYSLTIS
SLEYEDMGIYYCLQYDEFPLTFGAGTKLELK

>VL.17; SEQ ID NO: 64
NIVMTQSPKSMSMSVGERVTLTCKASENVGTYVSWYQQKPEQSPKLLIYGASNRYTGVPDRFTGSGSATDFTLTI
SSVQAEDLADYHCGQSYSTPYTFGGGTKLEIK

>VL.18; SEQ ID NO: 65
DIVMTQSPASLAVSLGQRATISCRASENVDKYGNSFMHWYQQKPGQPPKLLIYRASELQWGVPDRFSGSGSGT
DFTLTISSLQAEDVAVYYCQRSNEVPWTFGQGTKLEIKRTVAHHHHHH

>VL.19; SEQ ID NO: 66
SEIVLTQSPATLSLSPGERATLSCRASQSISTFLAWYQHKPGQAPRLLIYDASTRATGVPARFSGSRSGTDFTLTISTL
EPEDFAVYYCQQRYNWPPYTFGQGTKVEIK

>VL.20; SEQ ID NO: 67
QSVLTQPVSVSGSPGQSITISCTGTSSNADTYNLVSWYQQRPGKAPKLMIYEGTKRPSGVSNRFSASKSATAASLT
ISGLQPEDEADYYCCSYATSRTLVFGGGTKLTVVGQP

>VL.21; SEQ ID NO: 68
NIVMTQSPKSMSMSVGERVTLTCKASENVVTYVSWYQQKPEQSPKLLIYGASNRYTGVPDRFTGSGSATDFTLTI
SSVQAEDLADYHCGQGYSYPYTFGGGTKLEIK

>VL.22; SEQ ID NO: 69
QIVLSQSPAILSASPGEKVTMTCRASSSVSYIHWFQQKPGSSPKPWIYATSNLASGVPVRFSGSGSGTSYSLTISRV
EAEDAATYYCQQWTSNPPTFGGGTKLEIK

>VL.23; SEQ ID NO: 70
DIVMTQTPLSLPVTPGEPASISCRSSKSLLHSNGITYLYWYLQKPGQSPQLLIYQMSNLVSGVPDRFSGSGSGTDFT
LKISRVEAEDVGVYYCAQNLELPYTFGGGTKVEIK

>VL.24; SEQ ID NO: 71
QSVLTQPPSVSAAPGQKVTISCSGSSSNIGNDYVSWYQQLPGTAPKLLIYDNNKRPSGIPDRFSGSKSGTSATLGIT
GLQTGDEANYYCATWDRRPTAYVVFGGGTKLTVL

>VL.25; SEQ ID NO: 72
QSALTQPASVSGSPGQSITISCTGTSSDVGGYNYVSWYQQHPGKAPKLMIYDVSNRPSGVSNRFSGSKSGNTAS
LTISGLQAEDEADYYCSSYTSSSTRVFGTGTKVTVL

>VL.26; SEQ ID NO: 73
DIQMTQSPSTLSASVGDRVTITCSASSRVGYMHWYQQKPGKAPKLLIYDTSKLASGVPSRFSGSGSGTEFTLTISSL
QPDDFATYYCFQGSGYPFTFGGGTKVEIK
```

An "isolated" substance means that it has been altered by the hand of man from the natural state. If an "isolated" substance presents in nature, it has been changed or removed from its original environment, or both. For example, a polypeptide naturally present in a living subject is not "isolated" but the polypeptide is isolated if it has been substantially separated from the coexisting materials of its natural state and/or exists in a substantially pure state.

The term "specifically binds" or "specifically binding" refers to a non-random binding reaction between two molecules, such as the binding of the antibody or antigen-binding portion thereof to an epitope of the antigen. An antibody or antigen-binding portion thereof that "specifically binds" to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen or an epitope than it does with alternative targets/epitopes. An antibody or antigen-binding portion thereof "specifically binds" to a target antigen if it binds with greater affinity, avidity, more readily, and/or with greater duration than it binds to other substances. In certain embodiments, an antibody is said to specifically bind an antigen when it preferentially recognizes its target antigen in a complex mixture of proteins and/or macromolecules.

An "epitope" is a region of an antigen that is bound by an antibody. The term includes any polypeptide determinant capable of specific binding to an immunoglobulin. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics.

As used herein, the term "neutralizing" refers to neutralization of an activity, such as a biological activity, of a target protein (e.g., Yellow Fever Virus E-protein). In one embodiment, a neutralizing antibody binds to the E-DII epitope of Yellow Fever Virus E-protein and results in inhibition of a biological activity of Yellow Fever Virus and/or prevents the virus from infecting cells.

Subjects may be human, but also include other mammals, particularly those mammals useful as laboratory models for human disease, e.g. mouse, rat, rabbit, dog, etc.

The term "treat", "treatment" or "treating" refers to an action, application or therapy, wherein a subject, including a human being, is subjected to medical aid with the purpose of improving the subject's condition, directly or indirectly. Particularly, the term refers to reducing incidence, or alleviating one or more symptoms, eliminating recurrence, preventing recurrence, preventing incidence, improving one or more symptoms, and/or improving prognosis or a combination thereof in some embodiments. The skilled artisan would understand that treatment does not necessarily result in the complete absence or removal of symptoms. For example, with respect to Yellow Fever Virus, "treatment" or "treating" may refer to reducing the severity or duration of acute viral haemorrhagic disease caused by Yellow Fever.

An "effective amount" or an "effective dose" or a "therapeutically effective amount" in connection with administration of a pharmacological agent, as used herein, refers to an amount of a drug or pharmaceutical agent (e.g., an antibody or antigen-binding fragment or portion thereof, or a composition comprising the same) which, as compared to a corresponding subject who has not received such amount, results in an intended pharmacological result, or an effect in treatment, healing, prevention, or amelioration of a disease or disease symptom, disorder, or side effect, or a decrease in the rate of advancement of a disease or disorder, or any symptom thereof. The effective amount or dose of a pharmacological agent may vary depending on the particular active ingredient employed, the mode of administration, and/or the age, size, and condition of the subject to be treated.

The present disclosure also provides compositions (e.g., pharmaceutical compositions) comprising an antibody or antigen-binding portion thereof that binds specifically to the E-DII epitope of Yellow Fever Virus E-protein. In some embodiments, the E-DII epitope comprises an asparagine at position 106, a lysine at position 93, and a lysine at position 104 of Yellow Fever Virus E-protein. Compositions can be prepared from any one of the antibodies or antigen-binding portions described herein. The antibodies or antigen-binding portions thereof, as well as the encoding nucleic acids or nucleic acid sets, vectors comprising such, or host cells comprising the vectors, as described herein can be mixed with a pharmaceutically acceptable carrier (excipient), such as to form a pharmaceutical composition for use in treating a target disease. Pharmaceutically acceptable excipients (carriers) including buffers, are well known in the art. See, e.g., Remington: The Science and Practice of Pharmacy 20th Ed. (2000) Lippincott Williams and Wilkins, Ed. K. E. Hoover.

The pharmaceutical compositions can comprise pharmaceutically acceptable carriers, excipients, or stabilizers in the form of lyophilized formulations or aqueous solutions. (Remington: The Science and Practice of Pharmacy $20^{th}$ Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ (polysorbate), PLURONICS™ (poloxamers) or polyethylene glycol (PEG).

The phrase "pharmaceutically acceptable", as used in connection with compositions of the present disclosure, refers to molecular entities and other ingredients of such compositions that are physiologically tolerable and do not typically produce untoward reactions when administered to a subject. Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans. "Acceptable" means that the carrier is compatible with the active ingredient of the composition (e.g., the nucleic acids, vectors, cells, or therapeutic antibodies) and does not negatively affect the subject to which the composition(s) are administered. Any of the pharmaceutical compositions to be used in the present methods can comprise pharmaceutically acceptable carriers, excipients, or stabilizers in the form of lyophilized formations or aqueous solutions.

Pharmaceutically acceptable carriers, including buffers, are well known in the art, and may comprise phosphate, citrate, and other organic acids; antioxidants including ascorbic acid and methionine; preservatives; low molecular weight polypeptides; proteins, such as serum albumin, gelatin, or immunoglobulins; amino acids; hydrophobic polymers; monosaccharides; disaccharides; and other carbohydrates; metal complexes; and/or non-ionic surfactants. See, e.g. Remington: The Science and Practice of Pharmacy $20^{th}$ Ed. (2000) Lippincott Williams and Wilkins, Ed. K. E. Hoover.

A pharmaceutical composition can be presented in unit dosage form and can be prepared by any suitable method, many of which are well-known. Such methods can include the step of bringing an anti-YFV antibody into association with a carrier that constitutes one or more accessory ingredients.

Compositions provided herein can be a sterile aqueous preparation, which preferably in some embodiments is isotonic with the blood of the recipient. This aqueous preparation can be formulated according to known methods using suitable dispersing or wetting agents and suspending agents. The sterile aqueous preparations also can be a sterile injectable solution or suspension in a non-toxic parenterally-acceptable diluent or solvent. Among the acceptable vehicles and solvents that can be employed are water, Ringer's solution, and isotonic sodium chloride solution.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Moreover, vectors may be capable of directing the expression of genes to which they are operatively linked. Such vectors are referred to herein as "recombinant expression vectors" or "expression vectors".

The term "recombinant host cell" or "host cell", as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein.

Examples

Anti-YFV monoclonal antibodies are designed using structure-guided analysis of the YFV envelope protein epitopes, focusing on the envelope domain II fusion loop. Mutationally constrained epitope(s) on the surface of the yellow fever virus are identified. Appropriate antibody scaffolds that satisfy the epitope-paratope constraints are then identified, and the antibodies to target and neutralize the virus are engineered.

Anti-YFV antibodies are cloned, expressed and purified using known methods, and screened for expression and biophysical properties. The in silico designed antibodies are cloned in mammalian expression vectors and purified for further analysis. Both expression as well as various analytical parameters indicative of purity and stability are assessed. The potency of the antibodies against yellow fever virus is evaluated using in vitro and in vivo models of infection.

In vitro neutralization potency of engineered antibodies are assessed against the YF17D-204 vaccine strain of the yellow fever virus, using a plaque reduction neutralization test (PRNT). For selected antibodies, additional evaluation of potency are conducted using murine models of YFV infection.

Rational Design of Anti-YF mAbs

Promising anti-YFV monoclonal antibodies must neutralize a broad range of strains and target regions that are associated with robust protection. Epitopes play a critical role in the efficacy of a therapeutic antibody. In YFV infection, the envelope (E) protein is the predominant target of neutralizing antibodies. In order to define promising epitopes, a structure-guided analysis of the whole YFV assembly was conducted to identify spatially clustered, solvent accessible and sequence-conserved residues. This was done by mapping the sequence conservation scores (computed from an alignment of YFV envelope protein sequences) onto the homology model of a whole YFV E-protein assembly. Residues that have sequence conservation greater than 70% and solvent accessible surface area >40% were considered as putative epitope residues. From this analysis, the region proximal to the domain II (E-DII) hydrophobic fusion loop appeared highly accessible and conserved across YFV strains.

In order to engineer antibodies against the E-DII epitope, a structure-guided search for Fv scaffolds that recognize highly homologous epitope surfaces was conducted. Promising scaffolds were docked against the epitope (using the software ZRANK) and rank-ordered based on shape complementarity (>0.6), buried surface area (1,000 Sq. A°) and potential to make contacts with the critical E-DII epitope residues (N106, K93 and K104 of E-protein; numbering correspond to primary sequence of 17D YF vaccine strain). Then, the CDR loops of the top ranking scaffolds were redesigned through Rosetta Antibody Design to make optimal contacts with the epitope. The engineered antibodies were screened for in vitro neutralization of YFV.

Synthetic DNA sequences encoding the VH and VL domains provided in Tables 1 and 2 were cloned in frame with an IgG1 constant region, into mammalian expression vector and various combinations of the heavy and light chains combined into at least one hundred and ten YFV antibodies. Examples of such combinations are shown in Table 3 below.

TABLE 3

YF antibody combinations

|  | pVL.0 | pVL.1 | pVL.1.1 | pVL.1.2 | pVL.1.3 | pVL.1.4 | pVL.2 | pVL.3 | pVL.4 | pVL.5 | pVL.6 |
|---|---|---|---|---|---|---|---|---|---|---|---|
| pVH.0 | 1 | 2 |  |  |  |  | 3 | 4 |  |  |  |
| pVH.1 | 5 | 6 |  |  |  |  | 7 | 8 |  |  |  |
| pVH.2 | 9 | 10 |  |  |  |  | 11 | 12 |  |  |  |
| pVH.3 | 13 | 14 |  |  |  |  | 15 | 16 |  |  |  |
| pVH.3.1 |  |  | 22 | 23 | 24 | 25 |  |  |  |  |  |
| pVH.3.2 |  |  | 26 | 27 | 28 | 29 |  |  |  |  |  |
| pVH.4 |  |  |  |  |  |  |  |  | 18 |  |  |
| pVH.5 |  |  |  |  |  |  |  |  | 19 |  |  |
| pVH.6 |  |  |  |  |  |  |  |  |  | 20 |  |
| pVH.7 |  |  |  |  |  |  |  |  |  |  | 21 |

Illustrative Examples of Expression Levels and Biophysical Properties

A subset of YFV antibodies were purified from larger scale transfections in Expi293 cells. Proteins from cell culture supernatants were purified using the HiTrap Protein A column. Following dialysis, the protein concentration was estimated by nanodrop using theoretical extinction coefficients. The yields of various antibodies are summarized in Table 4.

TABLE 4

Yield of YF mAbs expressed in Expi293 cells

| mAb | Expression mg/L |
|---|---|
| 1 | 34.4 |
| 2 | 171 |
| 3 | 65.8 |

Additionally, purity and stability of various antibodies were determined by (1) UV spectrometry, (2) size exclusion chromatography, (3) microfluidic capillary electrophoresis and (4) thermal shift dye disassociation assay, respectively. Illustrative examples of such analytical biophysical parameters are summarized in Table 5 below.

TABLE 5

Purity and Stability of Select YF antibodies

|  | 1 | 2 |
|---|---|---|
| Abs maxima 1 (nm) | 228 | 228 |
| Abs maxima 2 (nm) | 278 | 279 |
| E1% (g/100 mL) | 14.2 | 13.8 |

TABLE 5-continued

Purity and Stability of Select YF antibodies

| | | | 1 | 2 |
|---|---|---|---|---|
| HMW-1 (%) | | | 0.16 | 0 |
| HMW-2 (%) | | | 0.68 | 0.62 |
| Monomer (%) | | | 99.04 | 98.99 |
| LMW (%) | | | 0.12 | 0.39 |
| Reduced | LC | Size (kDa) | 26.3 | 26.1 |
| | | % of total | 30.6 | 30.5 |
| | HC | Size (kDa) | 58.5 | 58.4 |
| | | % of total | 68.7 | 69.5 |
| Intact | | Size (kDa) | 154.7 | 154.8 |
| | | % of total | 88.0 | 87.0 |
| Melting temperature $T_m$ (° C.) | | | 69.0 | 69.1 |

Additional characterization of the glycoforms of various antibodies were determined by procainamide-label assisted LC-FLD-MS. Illustrative examples of glycosylation profiles observed are below (Table 6).

TABLE 6

Glycosylation Profiles

| Glycan | 1 (%) | 2 (%) |
|---|---|---|
| Man5 | 0.8 ± 0.01 | 1.2 ± 0.07 |
| G0 | 0.3 ± 0.00 | 0.5 ± 0.03 |
| G0F | 42.9 ± 0.05 | 51.6 ± 1.27 |
| G1 | 0.1 ± 0.00 | 0.2 ± 0.02 |
| G1F | 29.4 ± 0.14 | 25.2 ± 0.12 |
| G1'F | 15.8 ± 0.04 | 15.3 ± 0.70 |
| G2F | 10.5 ± 0.12 | 6.0 ± 0.32 |
| A1F | 0.2 ± 0.00 | 0.1 ± 0.01 |

Illustrative Examples of Neutralization Potency of Engineered Antibodies Against YF-17D Plaque Reduction Neutralization Test (PRNT) was conducted to determine the neutralization efficacy of the YFV antibodies against the YFV (17D-204). Vero cells were infected with either virus alone, no virus or virus pre-incubated with various dilutions of YFV antibodies. Plates were incubated for 7 days, fixed and stained with crystal violet to visualize plaque formations. Neutralization curves were generated using the Prism software (FIG. 1) and the 50% effective concentration (EC50) values were calculated by nonlinear regression using a variable slope (Table 6). The neutralization efficacy of an antibody is directly proportional to plaque reduction and the potency is depicted as concentration at which 50% of the virus particles are neutralized. The antibodies were highly potent in neutralizing the virus and illustrative examples are shown below in Table 7.

TABLE 7

Summary of EC50 values for YF mAbs

| mAb | EC50 (µg/ml) | STDEV |
|---|---|---|
| 1 | 0.012 | 0.006 |
| 2 | 0.007 | 0.002 |
| 3 | 0.011 | 0.010 |

Illustrative Examples of In Vivo Efficacy

FIG. 1 provides an illustrative example of in vivo efficacy of engineered antibodies against YF-17D-204 in a mouse model of infection. Efficacy of designed antibodies was tested in a lethal model of Yellow fever infection in AG129 mice. Protective efficacy of antibodies was tested in prophylaxis or as therapy as indicated in FIG. 1.

Figure 2A:
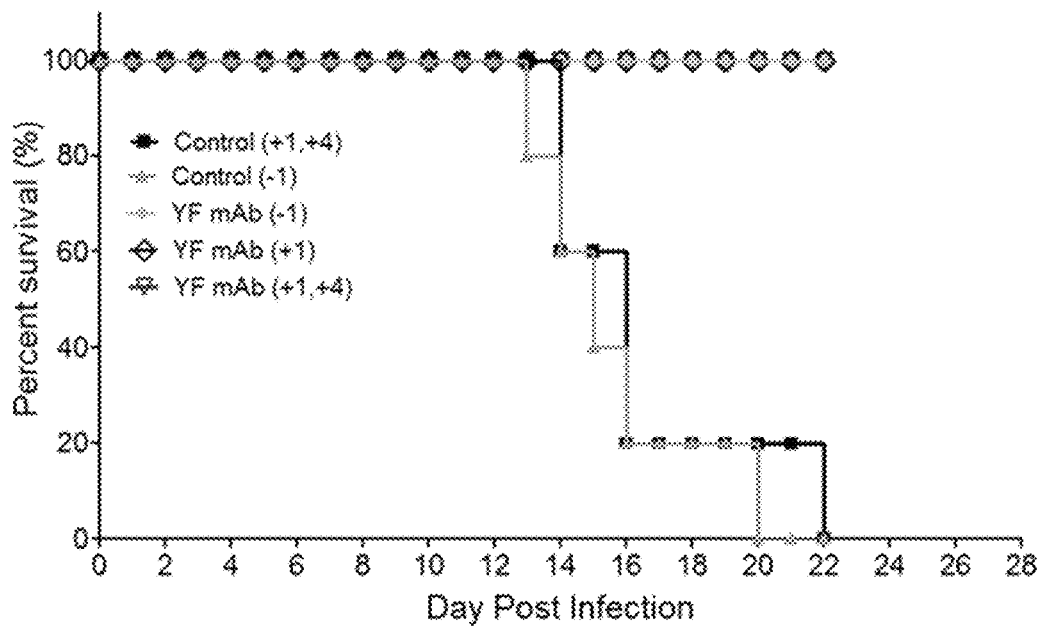
FIGS. 2A-2B shows in vivo efficacy of designed mAb against Yellow Fever Virus.
Figure 2B:
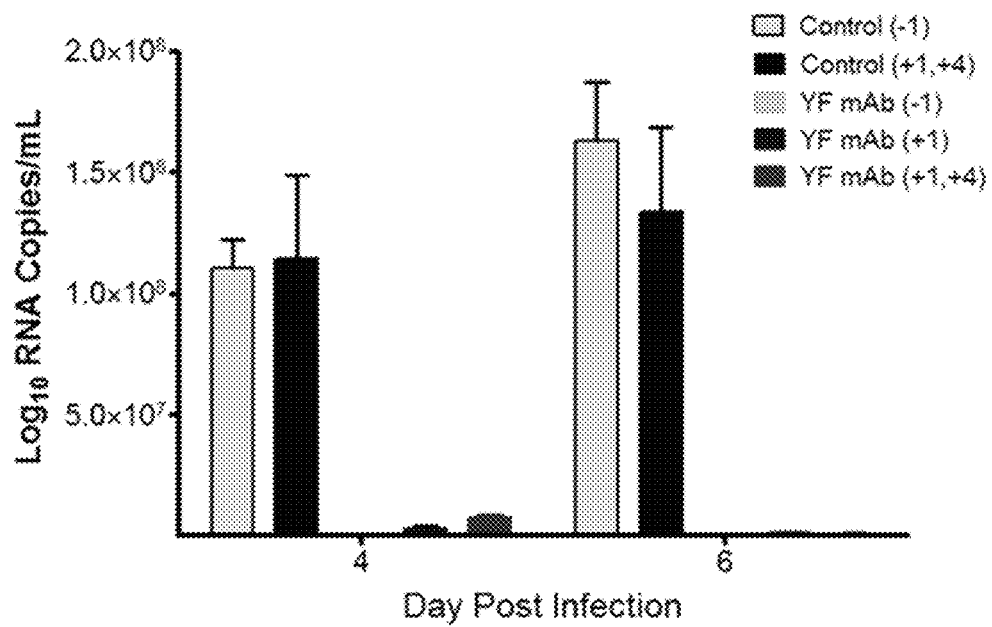

An illustrative example shown in FIG. 2, administration of antibody resulted in complete protection compared to control groups (FIG. 2A). Administration of antibody also led to greater than 2 $Log_{10}$ reduction in viremia at days 4 and 6 post infection (FIG. 2B).

What is claimed is:

1. An antibody or antigen-binding portion thereof, wherein said antibody or antigen-binding portion thereof binds to an E-DII epitope of Yellow Fever Virus, and wherein the antibody or antigen-binding portion thereof comprises: a) the three CDRs of the heavy chain variable region (VH) as set forth in SEQ ID NO: 4; and the three CDRs of the light chain variable region (VL) as set forth in SEQ ID NO: 38.

2. The antibody or antigen-binding portion thereof of claim 1, wherein the antibody or antigen-binding portion thereof comprises a VH as set forth in SEQ ID NO: 4, and a VL as set forth in SEQ ID NO: 38.

3. The antibody or antigen-binding portion thereof of claim 1, wherein the antibody or antigen-binding portion thereof is a monoclonal antibody, a chimeric antibody, or a humanized antibody.

4. The antibody or antigen-binding portion thereof of claim 1, wherein the antibody is a single chain antibody, a F(ab')2 fragment, a dAb fragment, a Fab fragment, or a Fv fragment.

5. The antibody or antigen-binding portion thereof of claim 1, wherein the antibody is an isolated antibody.

6. A composition comprising an antibody or antigen-binding portion thereof of claim 1 and a carrier.

7. The composition of claim 6, wherein the composition is a pharmaceutical composition that comprises a pharmaceutically acceptable carrier.

8. An antibody or antigen-binding portion thereof of claim 1 for use in a medicament.

9. A method for treating Yellow Fever, or a disease or condition associated with Yellow Fever Virus, comprising administering to a subject in need thereof a therapeutically effective amount of an antibody or antigen-binding portion thereof of claim 1.

10. A nucleic acid comprising a nucleotide sequence(s) encoding the antibody or antigen-binding portion thereof of claim 1.

11. A vector comprising the nucleic acid of claim 10.

12. The vector of claim 11, wherein the vector is an expression vector.

13. A host cell comprising the nucleic acid of claim 10.

14. A method of producing an antibody or antigen-binding portion thereof that binds to Yellow Fever Virus E-protein, comprising: culturing the host cell of claim 13 under conditions allowing for expression of the antibody or antigen-binding portion thereof.

15. The method of claim 14, further comprising harvesting the antibody or antigen-binding portion thereof.

16. The method of claim 14, wherein the antibody or antigen-binding portion thereof binds to the E-DII epitope of Yellow Fever Virus E-protein.

17. A host cell comprising the vector of claim 11.

* * * * *

SEQUENCE LISTING

```
<160> NUMBER OF SEQ ID NOS: 73

<210> SEQ ID NO 1
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 1

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Thr Asn Tyr
            20                  25                  30

Ala Met Ser Trp Val Arg Gln Thr Pro Glu Lys Arg Leu Glu Trp Val
        35                  40                  45

Ala Ser Ile Ser Ser Gly His Thr Pro Tyr Tyr Pro Asp Ser Val Lys
    50                  55                  60

Gly Arg Phe Thr Ile Ser Arg Asp Asn Ala Arg Asn Ile Leu Phe Leu
65                  70                  75                  80

Gln Met Ser Ser Leu Arg Ser Glu Asp Thr Ala Met Tyr Tyr Cys Ala
            85                  90                  95

Arg Gly Asp Tyr Tyr Gly Ser Val Tyr Ser Ala Met Asp Tyr Trp Gly
```

```
                    100                 105                 110

Gln Gly Thr Ser Val Thr Val Ser Ser
        115                 120

<210> SEQ ID NO 2
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Thr Asn Tyr
            20                  25                  30

Ala Met Ser Trp Val Arg Gln Ala Pro Gly Lys Gly Leu Glu Trp Val
        35                  40                  45

Ser Ser Ile Ser Ser Gly His Thr Pro Tyr Tyr Pro Asp Ser Val Lys
    50                  55                  60

Gly Arg Phe Thr Ile Ser Arg Asp Asn Ala Lys Lys Ser Leu Tyr Leu
65                  70                  75                  80

Gln Met Asn Ser Leu Arg Ala Glu Asp Thr Ala Leu Tyr Tyr Cys Ala
                85                  90                  95

Arg Gly Asp Tyr Tyr Gly Ser Val Tyr Ser Ala Met Asp Tyr Trp Gly
            100                 105                 110

Gln Gly Thr Thr Val Thr Val Ser Ser
        115                 120

<210> SEQ ID NO 3
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 3

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Val
        35                  40                  45

Ser Ser Ile Ser Ser Gly His Thr Pro Tyr Tyr Pro Asp Ser Val Lys
    50                  55                  60

Asp Arg Phe Thr Ile Ser Arg Asp Asn Ala Lys Lys Ser Leu Tyr Leu
65                  70                  75                  80

Gln Met Asn Ser Leu Arg Ala Glu Asp Thr Ala Leu Tyr Tyr Cys Ala
                85                  90                  95

Arg Gly Asp Tyr Tyr Gly Thr Val Tyr Ser Ala Met Asp Tyr Trp Gly
            100                 105                 110

Gln Gly Thr Thr Val Thr Val Ser Ser
        115                 120

<210> SEQ ID NO 4
<211> LENGTH: 121
<212> TYPE: PRT
<213> ORGANISM: Artificial Sequence
<220> FEATURE:
```

<223> OTHER INFORMATION: Synthetic Polypeptide

<400> SEQUENCE: 4

Glu Val Gln Leu Val Glu Ser Gly Gly Gly Leu Val Gln Pro Gly Arg
1               5                   10                  15

Ser Leu Arg Leu Ser Cys Ala Ala Ser Gly Tyr Ala Phe Thr Asn Tyr
            20                  25                  30

Ala Met Ser Trp Val Arg Gln Ala Pro Gly Lys Gly Leu Glu Trp Val
        35                  40                  45

Ser Ser Ile Ser Ser Gly His Thr Pro Tyr Tyr Pro Asp Thr Val Lys
    50                  55                  60

Gly Arg Phe Thr Ile Ser Arg Asp Asn Ala Lys Lys Ser Leu Tyr Leu
65                  70                  75                  80

Gln Met Asn Ser Leu Arg Ala Glu Asp Thr Ala Leu Tyr Tyr Cys Ala
                85                  90                  95

Arg Gly Asp Tyr Tyr Gly Ser Ser Tyr Ser Ala Met Asp Tyr Trp Gly
            100                 105                 110

Gln Gly Thr Thr Val Thr Val Ser Ser
        115                 120

<210> SEQ ID NO 5
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 5

Glu Val Gln Leu Val Glu Ser Gly Gly Gly Leu Val Gln Pro Gly Arg
1               5                   10                  15

Ser Leu Arg Leu Ser Cys Ala Ala Ser Gly Tyr Ala Phe Thr Asn Tyr
            20                  25                  30

Gly Val Asn Trp Val Arg Gln Ala Pro Gly Lys Gly Leu Glu Trp Val
        35                  40                  45

Ser Ser Ile Ser Ser Gly Gly Ser Thr Tyr Tyr Pro Asp Ser Val Lys
    50                  55                  60

Gly Arg Phe Thr Ile Ser Arg Asp Asn Ala Lys Lys Ser Leu Tyr Leu
65                  70                  75                  80

Gln Met Asn Ser Leu Arg Ala Glu Asp Thr Ala Leu Tyr Tyr Cys Ala
                85                  90                  95

Arg His Asp Tyr Tyr Gly Ser Ser Tyr Ala Met Asp Tyr Trp Gly Gln
            100                 105                 110

Gly Thr Thr Val Thr Val Ser Ser
        115                 120

<210> SEQ ID NO 6
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 6

Glu Val Gln Leu Val Glu Ser Gly Gly Gly Leu Val Gln Pro Gly Arg
1               5                   10                  15

Ser Leu Arg Leu Ser Cys Ala Ala Ser Gly Tyr Ala Phe Thr Asn Tyr
            20                  25                  30

Gly Val Asn Trp Val Arg Gln Ala Pro Gly Lys Gly Leu Glu Trp Val 35                  40                  45

Ser Ser Ile Ser Ser Gly Gly Ser Thr Tyr Tyr Pro Asp Ser Val Lys
            50                  55                  60

Gly Arg Phe Thr Ile Ser Arg Asp Asn Ala Lys Lys Ser Leu Tyr Leu
65                  70                  75                  80

Gln Met Asn Ser Leu Arg Ala Glu Asp Thr Ala Leu Tyr Tyr Cys Ala
                85                  90                  95

Arg Ser His Tyr Tyr Gly Ser Ser Tyr Asp Ala Met Asp Tyr Trp Gly
                    100                 105                 110

Gln Gly Thr Thr Val Thr Val Ser Ser
            115                 120

<210> SEQ ID NO 7
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 7

Glu Val Gln Leu Val Glu Ser Gly Ala Glu Val Lys Lys Pro Gly Ser
1               5                   10                  15

Ser Val Lys Val Ser Cys Lys Ala Ser Gly Phe Thr Phe Thr Asn Tyr
                20                  25                  30

Ala Met Ser Trp Val Arg Gln Ala Pro Gly Gln Gly Pro Glu Trp Met
            35                  40                  45

Gly Ser Ile Ser Ser Gly His Thr Pro Tyr Tyr Pro Asp Ser Val Lys
        50                  55                  60

Gly Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Arg Gly Asp Tyr Tyr Gly Ser Val Tyr Ser Ala Met Asp Tyr Trp Gly
                100                 105                 110

Lys Gly Thr Thr Val Thr Val Ser Ser
            115                 120

<210> SEQ ID NO 8
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 8

Glu Val Gln Leu Val Glu Ser Gly Ala Glu Val Lys Lys Pro Gly Ser
1               5                   10                  15

Ser Val Lys Val Ser Cys Lys Ala Ser Gly Phe Thr Phe Thr Asn Tyr
                20                  25                  30

Ala Met Ser Trp Val Arg Gln Ala Pro Gly Gln Gly Pro Glu Trp Met
            35                  40                  45

Gly Ser Ile Ser Ser Gly His Thr Pro Tyr Tyr Pro Asp Ser Val Lys
        50                  55                  60

Gly Arg Val Thr Ile Thr Ala Asp Asp Phe Ala Gly Thr Val Tyr Met
65                  70                  75                  80

Glu Leu Ser Ser Leu Arg Ser Glu Asp Thr Ala Met Tyr Tyr Cys Ala
                85                  90                  95

```
Arg Gly Asp Tyr Tyr Gly Ser Val Tyr Ser Ala Met Asp Tyr Trp Gly
                100                 105                 110

Lys Gly Thr Thr Val Thr Val Ser Ser
        115                 120

<210> SEQ ID NO 9
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Gly Phe Thr Phe Thr Asn Tyr Ala
            20                  25                  30

Met Ser Trp Val Arg Gln Ala Pro Glu Gln Gly Leu Glu Trp Met Gly
        35                  40                  45

Ser Ile Ser Ser Gly His Thr Pro Tyr Tyr Pro Asp Ser Val Lys Gly
    50                  55                  60

Arg Val Thr Met Thr Ala Asp Thr Ser Thr Asn Thr Ala Tyr Met Glu
65                  70                  75                  80

Leu Arg Ser Leu Arg Ser Asp Asp Thr Ala Val Tyr Tyr Cys Ala Arg
                85                  90                  95

Gly Asp Tyr Tyr Gly Ser Val Tyr Ser Ala Met Asp Tyr Trp Gly Gln
                100                 105                 110

Gly Thr Leu Val Thr Val Ser Ser
        115                 120

<210> SEQ ID NO 10
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Thr Asn Tyr
            20                  25                  30

Ala Met Ser Trp Val Arg Gln Ala Pro Gly Lys Gly Leu Glu Tyr Val
        35                  40                  45

Ser Ser Ile Ser Ser Gly His Thr Pro Tyr Tyr Pro Asp Ser Val Lys
    50                  55                  60

Gly Arg Phe Thr Ile Ser Arg Asp Asn Ser Lys Asn Thr Leu Tyr Phe
65                  70                  75                  80

Glu Met Asn Ser Leu Arg Pro Glu Asp Thr Ala Val Tyr Tyr Cys Val
                85                  90                  95

Arg Gly Asp Tyr Tyr Gly Ser Val Tyr Ser Ala Met Asp Tyr Trp Gly
                100                 105                 110

Gln Gly Thr Thr Val Thr Val Ser Ser
        115                 120

<210> SEQ ID NO 11
<211> LENGTH: 122
<212> TYPE: PRT
<213> ORGANISM: Artificial Sequence
```

```
<220> FEATURE:
<223> OTHER INFORMATION: Synthetic Polypeptide

<400> SEQUENCE: 11

Ala Ser Val Leu Ser Glu Val Gln Leu Gln Gln Ser Gly Pro Glu Leu
1               5                   10                  15

Val Lys Pro Gly Ala Ser Val Lys Leu Ser Cys Lys Thr Ser Glu Asn
            20                  25                  30

Thr Phe Thr Glu Tyr Thr Met His Trp Val Lys Gln Ser His Gly Lys
        35                  40                  45

Ser Leu Glu Trp Ile Gly Gly Ile Asp Pro Asn Asn Gly Gly Thr Asn
    50                  55                  60

Tyr Asn Gln Lys Phe Lys Gly Lys Ala Thr Leu Thr Val Asp Lys Ser
65                  70                  75                  80

Ser Asn Thr Ala Tyr Met Glu Leu Arg Ser Leu Thr Ser Glu Asp Ser
                85                  90                  95

Ala Val Tyr Tyr Cys Gly Arg Arg Asp Tyr Tyr Ala Leu Asp Tyr Trp
            100                 105                 110

Gly Gln Gly Thr Ser Val Thr Val Ala Ser
        115                 120

<210> SEQ ID NO 12
<211> LENGTH: 117
<212> TYPE: PRT
<213> ORGANISM: Artificial Sequence
<220> FEATURE:
<223> OTHER INFORMATION: Synthetic Polypeptide

<400> SEQUENCE: 12

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Leu Arg Pro Gly Gln Gly Phe Glu Trp Ile
        35                  40                  45

Gly Asp Ile Asn Pro Asn Asn Gly Gly Pro Ser Tyr Asn Glu Lys Phe
    50                  55                  60

Lys Arg Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Ile Asp Asp Gly Tyr Arg Phe Gly Tyr Trp Gly Gln Gly Thr Leu
            100                 105                 110

Val Thr Val Ser Ala
        115

<210> SEQ ID NO 13
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 13

Gln Val Gln Leu Gln Gln Ser Gly Ser Glu Leu Met Lys Pro Gly Ala
1               5                   10                  15

Ser Val Gln Ile Ser Cys Lys Ala Thr Gly Tyr Thr Phe Ser Asp Tyr
            20                  25                  30
```

Trp Ile Glu Trp Val Lys Gln Arg Pro Gly His Gly Leu Glu Trp Ile
            35                  40                  45

Gly Asp Ile Leu Cys Gly Thr Gly Arg Thr Tyr Asn Glu Lys Leu
 50                  55                  60

Lys Ala Met Ala Thr Phe Thr Ala Asp Thr Ser Ser Asn Thr Ala Phe
 65                  70                  75                  80

Met Gln Leu Ser Ser Leu Thr Ser Glu Asp Ser Ala Val Tyr Tyr Cys
                 85                  90                  95

Ala Arg Ser Ala Ser Tyr Gly Asp Tyr Ala Asp Tyr Trp Gly His Gly
                100                 105                 110

Thr Thr Leu Thr Val Ser Ser
            115

<210> SEQ ID NO 14
<211> LENGTH: 115
<212> TYPE: PRT
<213> ORGANISM: Artificial Sequence
<220> FEATURE:
<223> OTHER INFORMATION: Synthetic Polypeptide

<400> SEQUENCE: 14

Ala Gln Leu Gln Gln Ser Gly Thr Gly Leu Ala Arg Pro Gly Ala Ser
 1               5                  10                  15

Val Lys Leu Ser Cys Lys Ala Ser Gly Tyr Thr Phe Thr Ser Tyr Gly
                 20                  25                  30

Ile Ser Trp Val Thr Gln Arg Ala Gly Gln Gly Leu Glu Trp Ile Gly
            35                  40                  45

Val Ile Tyr Pro Arg Ser Gly Asn Thr Tyr Tyr Asn Glu Lys Phe Arg
 50                  55                  60

Gly Lys Ala Thr Leu Thr Ala Asp Lys Ser Ser Ser Ala Tyr Met
 65                  70                  75                  80

Glu Leu Arg Gly Leu Thr Ala Glu Asp Ser Ala Val Tyr Phe Cys Ala
                 85                  90                  95

Arg Glu Asn Tyr Gly Ser Val Tyr Trp Gly Gln Gly Thr Thr Leu Thr
                100                 105                 110

Val Ser Ser
        115

<210> SEQ ID NO 15
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 15

Glu Val Gln Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys Asp Thr
                 20                  25                  30

Tyr Met His Trp Val Lys Gln Arg Pro Glu Gln Gly Leu Glu Trp Ile
            35                  40                  45

Gly Arg Ile Asp Pro Ala Asn Gly Tyr Ser Lys Tyr Asp Pro Lys Phe
 50                  55                  60

Gln Gly Lys Ala Thr Ile Thr Ala Asp Thr Ser Ser Asn Ala Ala Tyr
 65                  70                  75                  80

Leu Gln Leu Ser Ser Leu Thr Ser Glu Asp Thr Ala Val Tyr Phe Cys
                 85                  90                  95

```
Ala Arg Asp Tyr Glu Gly Phe Ala Tyr Trp Gly Gln Gly Thr Leu Val
            100                 105                 110

Thr Val Ser Ser
        115

<210> SEQ ID NO 16
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 16

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Thr Tyr Tyr Gly Asp Ser Val
    50                  55                  60

Lys Gly Arg Phe Thr Ile Ser Lys Asp Asn Ser Lys Lys Met Val Asn
65                  70                  75                  80

Leu Gln Met Asp Ser Leu Gly Val Glu Asp Thr Ala Phe Tyr Tyr Cys
                85                  90                  95

Ala Arg Gly Ile Ala Gly Gly Trp Ala Phe Trp Gly Ile Asp Leu Trp
            100                 105                 110

Gly Gln Gly Thr Leu Val Thr Val Ser Ser
        115                 120

<210> SEQ ID NO 17
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 17

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Tyr Ser Lys Tyr Asp Pro Lys Phe
    50                  55                  60

Gln Gly Lys Ala Thr Ile Thr Ala Asp Thr Ser Ser Asn Ala Ala Tyr
65                  70                  75                  80

Leu Gln Leu Ser Ser Leu Thr Ser Glu Asp Thr Ala Val Tyr Phe Cys
                85                  90                  95

Ala Arg Asp Tyr Glu Gly Phe Ala Tyr Trp Gly Gln Gly Thr Leu Val
            100                 105                 110

Thr Val Ser Ser
        115

<210> SEQ ID NO 18
<211> LENGTH: 123
<212> TYPE: PRT
```

<213> ORGANISM: Artificial Sequence
<220> FEATURE:
<223> OTHER INFORMATION: Synthetic Polypeptide

<400> SEQUENCE: 18

```
Glu Val Gln Leu Val Gln Ser Gly Ala Glu Val Arg Lys Pro Gly Ala
1               5                   10                  15

Ser Thr Lys Val Ser Cys Lys Ala Ser Gly Tyr Thr Phe Thr His Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Thr Tyr Ala Gln Lys Leu
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Trp Gly Ser Asn Tyr Val Trp Gly Ser Tyr Pro Lys Tyr
            100                 105                 110

Trp Gly Gln Gly Thr Leu Val Thr Val Ser Ser
        115                 120
```

<210> SEQ ID NO 19
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 19

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120
```

<210> SEQ ID NO 20
<211> LENGTH: 117
<212> TYPE: PRT
<213> ORGANISM: Artificial Sequence
<220> FEATURE:
<223> OTHER INFORMATION: Synthetic Polypeptide

<400> SEQUENCE: 20

```
Asp Val Gln Leu Val Glu Pro Gly Ala Glu Leu Val Gln Pro Gly Ala
1               5                   10                  15

Ser Val Lys Met Ser Cys Lys Ala Ser Gly Tyr Thr Phe Ser Ser Tyr
            20                  25                  30
```

-continued

Trp Ile Asn Trp Glu Lys Gln Arg Pro Gly Lys Gly Leu Glu Trp Ile
            35                  40                  45

Gly Asn Ile Tyr Pro Gly Ser Gly Thr Val Asn Tyr Asp Asp Lys Phe
        50                  55                  60

Lys Ser Lys Ala Thr Leu Thr Ile Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Thr Arg Gly Gly Ser His Ala Met Asp Tyr Trp Gly Gln Gly Thr Ser
            100                 105                 110

Val Thr Val Ser Ser
            115

<210> SEQ ID NO 21
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 21

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Ser Tyr Ser Asn His
            20                  25                  30

Trp Met His Trp Val Arg Gln Ala Pro Gly Lys Gly Leu Val Trp Val
            35                  40                  45

Ser Arg Ile Asn Ser Asp Gly Ser Thr Arg Asn Tyr Ala Asp Phe Val
        50                  55                  60

Lys Gly Arg Phe Thr Ile Ser Arg Asp Asn Ala Glu Asn Thr Leu Tyr
65                  70                  75                  80

Leu Glu Met Asn Ser Leu Thr Ala Asp Thr Ala Val Tyr Tyr Cys
                85                  90                  95

Val Arg Asp Gly Val Arg Phe Tyr Tyr Asp Ser Thr Gly Tyr Tyr Pro
            100                 105                 110

Asp Ser Phe Phe Lys Tyr Gly Met Asp Val Trp Gly Gln Gly Thr Thr
            115                 120                 125

Val Thr Val Ser Ser
            130

<210> SEQ ID NO 22
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 22

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Ser Tyr Ser Asn His
            20                  25                  30

Trp Met His Trp Val Arg Gln Ala Pro Gly Lys Gly Leu Val Trp Val
            35                  40                  45

Ser Arg Ile Asn Ser Asp Gly Ser Thr Arg Asn Tyr Ala Asp Phe Val
        50                  55                  60

Lys Gly Arg Phe Thr Ile Ser Arg Asp Asn Ala Glu Asn Thr Leu Tyr

```
                65                  70                  75                  80
Leu Glu Met Asn Ser Leu Thr Ala Asp Asp Thr Ala Val Tyr Tyr Cys
                85                  90                  95
Val Arg Asp Gly Val Arg Phe Tyr Tyr Asp Ser Thr Gly Tyr Tyr Pro
            100                 105                 110
Asp Ser Phe Phe Lys Tyr Gly Met Asp Val Trp Gly Gln Gly Thr Thr
            115                 120                 125
Val Thr Val Ser Ser
            130

<210> SEQ ID NO 23
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 23

Glu Val Lys Leu Val Glu Ser Gly Gly Gly Leu Val Leu Pro Gly Gly
1               5                   10                  15
Ser Leu Arg Leu Ser Cys Ala Thr Ser Gly Phe Thr Phe Thr Asp Tyr
            20                  25                  30
Tyr Met Thr Trp Val Arg Gln Pro Pro Gly Lys Ala Leu Glu Trp Leu
            35                  40                  45
Gly Phe Ile Gly Asn Lys Ala Asn Asp Tyr Thr Thr Glu Tyr Ser Ala
        50                  55                  60
Ser Val Lys Gly Arg Phe Thr Ile Ser Arg Asp Asp Ser Gln Ser Ile
65                  70                  75                  80
Leu Tyr Leu Gln Met Ser Thr Leu Arg Ala Glu Asp Arg Ala Thr Tyr
                85                  90                  95
Tyr Cys Ala Thr Val Tyr Gly Asn Tyr Pro Tyr Phe Asp Val Trp Gly
            100                 105                 110
Ala Gly Thr Thr Val Ala Val Ser Ser
            115                 120

<210> SEQ ID NO 24
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 24

Glu Val Gln Leu Val Glu Ser Gly Ala Glu Val Lys Lys Pro Gly Ser
1               5                   10                  15
Ser Val Lys Val Ser Cys Lys Ala Ser Gly Gly Thr Phe Asn Asn Tyr
            20                  25                  30
Ala Ile Ser Trp Val Arg Gln Ala Pro Gly Gln Gly Leu Glu Trp Met
            35                  40                  45
Gly Gly Ile Ile Pro Ile Phe Gly Gly Ala Asn Tyr Ala Gln Lys Phe
        50                  55                  60
Gln Gly Arg Val Thr Ile Thr Ala Asp Arg Ser Thr Ser Thr Val Tyr
65                  70                  75                  80
Met Glu Leu Ser Gly Leu Arg Ser Glu Asp Thr Ala Val Tyr Tyr Cys
                85                  90                  95
Ala Arg Arg Pro Gln Ser Ile Phe Asp Trp Asn Phe Asp Leu Trp Gly
            100                 105                 110
```

Arg Gly Thr Leu Val Thr Val Ser Ser Ala Gly Thr Lys Gly Pro Ser
          115                 120                 125

<210> SEQ ID NO 25
<211> LENGTH: 134
<212> TYPE: PRT
<213> ORGANISM: Artificial Sequence
<220> FEATURE:
<223> OTHER INFORMATION: Synthetic Polypeptide

<400> SEQUENCE: 25

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser His
            20                  25                  30

Trp Met His Trp Val Arg Gln Ala Pro Gly Lys Gly Leu Val Trp Val
        35                  40                  45

Ser Arg Thr Asn Ser Asp Gly Ser Ser Thr Ser Tyr Ala Asp Ser Val
    50                  55                  60

Lys Gly Arg Phe Met Ile Ser Arg Asp Asn Ser Lys Asn Thr Val Tyr
65                  70                  75                  80

Leu His Met Asn Gly Leu Arg Ala Glu Asp Thr Ala Val Tyr Phe Cys
                85                  90                  95

Ala Arg Asp Gly Val Arg Tyr Tyr Tyr Asp Ser Thr Gly Tyr Tyr Pro
            100                 105                 110

Asp Asn Phe Phe Gln Tyr Gly Leu Asp Val Trp Gly Gln Gly Thr Thr
        115                 120                 125

Val Thr Val Ser Ser Ala
        130

<210> SEQ ID NO 26
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 26

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ser His Gly Lys Ser Leu Glu Trp Val
        35                  40                  45

Gly Tyr Thr Tyr Pro Tyr Asn Gly Gly Ile Gly Tyr Asn Gln Lys Phe
    50                  55                  60

Lys Ser Lys Ala Thr Leu Thr Leu Asp Asn Ser Ser Arg Thr Ala Tyr
65                  70                  75                  80

Met Glu Leu Arg Ser Leu Thr Ser Glu Asp Ser Ala Val Tyr Tyr Cys
                85                  90                  95

Val Arg Arg Gly Tyr Arg Tyr Asp Gly Ala His Phe Asp Tyr Trp Gly
            100                 105                 110

Gln Gly Thr Thr Leu Thr Val Ser Ser
        115                 120

<210> SEQ ID NO 27
<211> LENGTH: 120
<212> TYPE: PRT
<213> ORGANISM: Artificial Sequence

```
<220> FEATURE:
<223> OTHER INFORMATION: Synthetic Polypeptide

<400> SEQUENCE: 27

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Leu His Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Trp Gly Asn Tyr Pro His Tyr Ala Met Asp Tyr Trp Gly Gln
            100                 105                 110

Gly Thr Ser Val Thr Val Ser Ser
        115                 120

<210> SEQ ID NO 28
<211> LENGTH: 115
<212> TYPE: PRT
<213> ORGANISM: Artificial Sequence
<220> FEATURE:
<223> OTHER INFORMATION: Synthetic Polypeptide

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Gly Phe Asn Ile Lys Asp Val Tyr
            20                  25                  30

Met Ser Trp Val Arg Gln Ala Pro Glu Gln Gly Leu Glu Trp Met Gly
        35                  40                  45

Arg Ile Asp Pro Glu Asn Gly Asp Thr Lys Tyr Asp Pro Lys Leu Gln
    50                  55                  60

Gly Arg Val Thr Met Thr Ala Asp Thr Ser Thr Asn Thr Ala Tyr Met
65                  70                  75                  80

Glu Leu Arg Ser Leu Arg Ser Asp Asp Thr Ala Val Tyr Tyr Cys Ala
                85                  90                  95

Arg Gly Trp Glu Gly Phe Ala Tyr Trp Gly Gln Gly Thr Leu Val Thr
            100                 105                 110

Val Ser Ser
        115

<210> SEQ ID NO 29
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30
```

-continued

Ser Met His Trp Val Arg Gln Ala Pro Gly Lys Gly Leu Glu Tyr Val
            35                  40                  45

Ser Ala Ile Thr Gly Glu Gly Asp Ser Ala Phe Tyr Ala Asp Ser Val
        50                  55                  60

Lys Gly Arg Phe Thr Ile Ser Arg Asp Asn Ser Lys Asn Thr Leu Tyr
 65                  70                  75                  80

Phe Glu Met Asn Ser Leu Arg Pro Glu Asp Thr Ala Val Tyr Tyr Cys
                85                  90                  95

Val Gly Gly Tyr Ser Asn Phe Tyr Tyr Tyr Thr Met Asp Val Trp
            100                 105                 110

Gly Gln Gly Thr Thr Val Thr Val Ser Ser Gly
        115                 120

<210> SEQ ID NO 30
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 30

Glu Val Gln Leu Val Glu Ser Gly Gly Gly Leu Val Arg Pro Gly Gly
 1               5                  10                  15

Ser Leu Arg Leu Ser Cys Ala Ala Ser Gly Phe Ser Tyr Ser Asn His
            20                  25                  30

Trp Met His Trp Val Arg Gln Ala Pro Gly Lys Gly Leu Val Trp Val
        35                  40                  45

Ser Arg Ile Asn Ser Asp Gly Ser Thr Arg Asn Tyr Ala Asp Phe Val
    50                  55                  60

Lys Gly Arg Phe Thr Ile Ser Arg Asp Asn Ala Glu Asn Thr Leu Tyr
 65                  70                  75                  80

Leu Glu Met Asn Ser Leu Thr Ala Asp Thr Ala Val Tyr Tyr Cys
                85                  90                  95

Val Arg Asp Gly Val Arg Phe Tyr Tyr Asp Ser Thr Gly Tyr Tyr Pro
            100                 105                 110

Asp Ser Phe Phe Lys Tyr Gly Met Asp Val Trp Gly Gln Gly Thr Thr
        115                 120                 125

Val Thr Val Ser Ser
    130

<210> SEQ ID NO 31
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 31

Asp Val Gln Leu Val Glu Ser Gly Gly Gly Leu Val Gln Pro Gly Gly
 1               5                  10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Leu His Tyr Ala Asp Thr Val
    50                  55                  60

Lys Gly Arg Phe Thr Ile Ser Arg Asp Asn Pro Lys Asn Thr Leu Phe
 65                  70                  75                  80

```
Leu Gln Met Thr Ser Leu Arg Ser Glu Asp Thr Ala Met Tyr Tyr Cys
                85                  90                  95

Ala Arg Trp Gly Asn Tyr Pro His Tyr Ala Met Asp Tyr Trp Gly Gln
            100                 105                 110

Gly Thr Ser Val Thr Val Ser Ser
        115                 120

<210> SEQ ID NO 32
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 32

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 33
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

```
<210> SEQ ID NO 34
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 34
```

Glu Val Gln Leu Val Glu Ser Gly Ala Glu Val Lys Pro Gly Ser
1               5                   10                  15

Ser Val Lys Val Ser Cys Lys Ala Gly Gly Pro Phe Arg Ser Tyr
            20                  25                  30

Ala Ile Ser Trp Val Arg Gln Ala Pro Gly Gln Gly Pro Glu Trp Met
        35                  40                  45

Gly Gly Ile Ile Pro Ile Phe Gly Thr Thr Lys Tyr Ala Pro Lys Phe
    50                  55                  60

Gln Gly Arg Val Thr Ile Thr Ala Asp Asp Phe Ala Gly Thr Val Tyr
65                  70                  75                  80

Met Glu Leu Ser Ser Leu Arg Ser Glu Asp Thr Ala Met Tyr Tyr Cys
                85                  90                  95

Ala Lys His Met Gly Tyr Gln Val Arg Glu Thr Met Asp Val Trp Gly
            100                 105                 110

Lys Gly Thr Thr Val Thr Val Ser Ser
        115                 120

```
<210> SEQ ID NO 35
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 35
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
        115                 120

```
<210> SEQ ID NO 36
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 36
```

Gln Val Thr Leu Arg Glu Ser Gly Pro Ala Leu Val Lys Pro Thr Gln
1               5                   10                  15

```
Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys His Tyr Asn Pro Ser
 50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                    85                  90                  95

Cys Ala Arg Asp Met Ile Phe Asn Phe Tyr Phe Asp Val Trp Gly Gln
                100                 105                 110

Gly Thr Thr Val Thr Val Ser Ser
            115                 120
```

<210> SEQ ID NO 37
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 37

```
Asp Ile Arg Met Thr Gln Ser Pro Ser Ser Met Tyr Ala Ser Leu Gly
 1               5                  10                  15

Glu Arg Val Thr Val Thr Cys Lys Ala Ser Gln Asp Ile Asn Ser Tyr
            20                  25                  30

Leu Ser Trp Leu Gln Gln Lys Pro Gly Lys Ser Pro Lys Thr Leu Ile
        35                  40                  45

Tyr Arg Ala Asn Arg Leu Phe Asp Gly Val Pro Ser Arg Phe Ser Gly
     50                  55                  60

Ser Gly Ser Gly Gln Asp Tyr Ser Leu Thr Ile Ser Ser Leu Glu Tyr
 65                  70                  75                  80

Glu Asp Met Gly Ile Phe Tyr Cys Leu Gln Tyr Asp Glu Phe Pro Phe
                    85                  90                  95

Thr Phe Gly Ser Gly Thr Lys Leu Glu Ile Lys
                100                 105
```

<210> SEQ ID NO 38
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 38

```
Asp Ile Arg Met Thr Gln Ser Pro Ser Ser Leu Ser Ala Ser Val Gly
 1               5                  10                  15

Asp Arg Val Thr Ile Thr Cys Lys Ala Ser Gln Asp Ile Asn Ser Tyr
            20                  25                  30

Leu Ser Trp Leu Gln Gln Lys Pro Gly Lys Ser Pro Lys Thr Leu Ile
        35                  40                  45

Tyr Arg Ala Asn Arg Leu Phe Asp Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Ile Tyr Tyr Cys Leu Gln Tyr Asp Glu Phe Pro Phe
```

```
            85                  90                  95
Thr Phe Gly Ser Gly Thr Lys Val Glu Ile Lys
            100                 105

<210> SEQ ID NO 39
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 39

Asp Ile Arg Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Asn Trp Leu Gln Gln Lys Pro Gly Lys Ser Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Tyr Asp Glu Phe Pro Tyr
                85                  90                  95

Thr Phe Gly Ser Gly Thr Lys Val Glu Ile Lys
            100                 105

<210> SEQ ID NO 40
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 40

Asp Ile Arg Met Thr Gln Ser Pro Ser Ser Leu Ser Ala Ser Val Gly
1               5                   10                  15

Asp Arg Val Thr Ile Thr Cys Lys Ala Ser Gln Asp Ile Lys Ser Tyr
            20                  25                  30

Leu Ser Trp Leu Gln Gln Lys Pro Gly Lys Ser Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Tyr Asp Glu Phe Pro Tyr
                85                  90                  95

Thr Phe Gly Ser Gly Thr Lys Val Glu Ile Lys
            100                 105

<210> SEQ ID NO 41
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 41

Asp Ile Arg Met Thr Gln Ser Pro Ser Ser Leu Ser Ala Ser Val Gly
1               5                   10                  15
```

Asp Arg Val Thr Ile Thr Cys Lys Ala Ser Gln Asp Ile Asn Ser Tyr
            20                  25                  30

Leu Asn Trp Leu Gln Gln Lys Pro Gly Lys Ser Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu His Tyr Asp Glu Phe Pro Tyr
                85                  90                  95

Thr Phe Gly Ser Gly Thr Lys Val Glu Ile Lys
            100                 105

<210> SEQ ID NO 42
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 42

Asp Ile Arg Met Thr Gln Ser Pro Ser Ser Leu Ser Ala Ser Val Gly
1               5                   10                  15

Asp Arg Val Thr Ile Thr Cys Lys Ala Ser Gln Asp Ile Lys Ser Tyr
            20                  25                  30

Leu Ser Trp Leu Gln Gln Lys Pro Gly Lys Ser Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu His Tyr Asp Glu Phe Pro Tyr
                85                  90                  95

Thr Phe Gly Ser Gly Thr Lys Val Glu Ile Lys
            100                 105

<210> SEQ ID NO 43
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 43

Asp Ile Arg Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Leu Gln Gln Lys Pro Gly Lys Ser Pro Lys Thr Leu Ile
        35                  40                  45

Tyr Arg Ala Asn Arg Leu Met Ile Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Tyr Asp Asp Phe Pro Leu
                85                  90                  95

Thr Phe Gly Ser Gly Thr Lys Val Glu Ile Lys

<210> SEQ ID NO 44
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 44

```
Asp Ile Arg Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Phe
            20                  25                  30

Leu Thr Trp Leu Gln Gln Lys Pro Gly Lys Ser Pro Lys Thr Leu Ile
        35                  40                  45

Tyr Arg Ala Asn Arg Val Phe Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Tyr Asp Asp Phe Pro Leu
                85                  90                  95

Thr Phe Gly Ser Gly Thr Lys Val Glu Ile Lys
            100                 105
```

<210> SEQ ID NO 45
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 45

```
Gln Ser Val Leu Thr Gln Pro Pro Ser Val Ser Ala Ala Pro Gly Gln
1               5                   10                  15

Lys Val Thr Ile Ser Cys Lys Ala Ser Gln Asp Ile Asn Ser Tyr Leu
            20                  25                  30

Ser Trp Tyr Gln Gln Leu Pro Gly Thr Ala Pro Lys Leu Leu Ile Tyr
        35                  40                  45

Arg Ala Asn Arg Leu Phe Asp Gly Ile Pro Asp Arg Phe Ser Gly Ser
    50                  55                  60

Lys Ser Gly Thr Ser Ala Thr Leu Gly Ile Thr Gly Leu Gln Thr Gly
65                  70                  75                  80

Asp Glu Ala Asn Tyr Tyr Cys Leu Gln Tyr Asp Glu Phe Pro Phe Thr
                85                  90                  95

Phe Gly Gly Gly Thr Lys Leu Thr Val Leu
            100                 105
```

<210> SEQ ID NO 46
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 46

```
Asp Ile Val Met Thr Gln Ser Pro Ala Ser Leu Ala Val Ser Leu Gly
1               5                   10                  15

Gln Arg Ala Thr Ile Ser Cys Lys Ala Ser Gln Asp Ile Asn Ser Tyr
            20                  25                  30
```

Leu Ser Trp Tyr Gln Gln Lys Pro Gly Gln Pro Pro Lys Leu Leu Ile
         35                  40                  45

Tyr Arg Ala Asn Arg Leu Phe Asp Gly Val Pro Asp Arg Phe Ser Gly
         50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Leu Gln Tyr Asp Glu Phe Pro Phe
                 85                  90                  95

Thr Phe Gly Gln Gly Thr Lys Leu Glu Ile Lys Arg
                100                 105

<210> SEQ ID NO 47
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 47

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Asp Ile Asn Ser Tyr
                 20                  25                  30

Leu Ser Trp Tyr Gln His Lys Pro Gly Gln Ala Pro Arg Leu Leu Ile
         35                  40                  45

Tyr Arg Ala Asn Arg Leu Phe Asp Gly Val Pro Ala Arg Phe Ser Gly
         50                  55                  60

Ser Arg Ser Gly Thr Asp Phe Thr Leu Thr Ile Ser Thr Leu Glu Pro
65                  70                  75                  80

Glu Asp Phe Ala Val Tyr Tyr Cys Gln Leu Gln Tyr Asp Glu Phe Pro
                 85                  90                  95

Phe Thr Phe Gly Gln Gly Thr Lys Val Glu Ile Lys
                100                 105

<210> SEQ ID NO 48
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 48

Asp Ile Val Met Thr Gln Ser Gln Lys Phe Met Ser Thr Ser Val Gly
1               5                   10                  15

Asp Arg Val Ser Ile Thr Cys Lys Ala Ser Gln His Val Gly Ser Ala
                 20                  25                  30

Val Ala Trp Tyr Gln Gln Lys Pro Gly Gln Ser Pro Thr Leu Leu Ile
         35                  40                  45

His Ser Ala Ser Asn Arg Tyr Thr Gly Val Pro Asp Arg Phe Thr Gly
         50                  55                  60

Ser Gly Ser Gly Thr Asp Phe Thr Leu Thr Ile Ser Asn Ile Gln Ser
65                  70                  75                  80

Glu Asp Leu Ala Asp Tyr Phe Cys Gln Gln Tyr Asn Ser Tyr Pro Thr
                 85                  90                  95

Phe Gly Gly Gly Thr Lys Leu Glu Ile Lys
                100                 105

-continued

```
<210> SEQ ID NO 49
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 49

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Ala
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Arg
                85                  90                  95

Thr Phe Gly Gly Gly Thr Lys Leu Glu Ile Lys Arg
            100                 105

<210> SEQ ID NO 50
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 50

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Ser Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Thr Thr Pro Leu
                85                  90                  95

Thr Phe Gly Ala Gly Thr Lys Leu Glu Leu Lys
            100                 105

<210> SEQ ID NO 51
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 51

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45
```

Tyr Ser Ala Ser Asn Arg Tyr Thr Gly Val Pro Asp Arg Phe Thr Gly
            50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Phe Ser Ser Tyr Pro Tyr
                85                  90                  95

Thr Phe Gly Gly Gly Thr Lys Leu Glu Ile Lys
            100                 105

<210> SEQ ID NO 52
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 52

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Val Arg Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Ser Leu Glu Ser Gly Ile Pro Thr
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Thr Asn
                85                  90                  95

Val Asp Pro Trp Ala Phe Gly Gly Gly Thr Lys Leu Glu Ile Lys
            100                 105                 110

<210> SEQ ID NO 53
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 53

Asp Val Val Met Thr Gln Ser Pro Gly Thr Leu Ser Leu Ser Pro Gly
1               5                   10                  15

Glu Arg Ala Thr Leu Ser Cys Arg Ala Ser Gln Asn Val Tyr Ser Tyr
            20                  25                  30

Leu Gly Trp Tyr Gln His Lys Pro Gly Arg Ser Pro Arg Leu Leu Ile
        35                  40                  45

Phe Gly Val Thr Ser Arg Ala Thr Gly Val Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Ala Gly Ser Ala Tyr
                85                  90                  95

Thr Phe Gly Gln Gly Thr Lys Val Glu Ile Lys Arg
            100                 105

<210> SEQ ID NO 54
<211> LENGTH: 111
<212> TYPE: PRT

```
<213> ORGANISM: Artificial Sequence
<220> FEATURE:
<223> OTHER INFORMATION: Synthetic Polypeptide

<400> SEQUENCE: 54

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Val Arg Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Ser Leu Glu Ser Gly Ile Pro Thr
50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Thr Asn
                85                  90                  95

Val Asp Pro Trp Ala Phe Gly Gly Gly Thr Lys Leu Glu Ile Lys
            100                 105                 110

<210> SEQ ID NO 55
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 55

Gln Ser Val Leu Thr Gln Pro Ser Ser Val Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Gly Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly
            100                 105                 110

<210> SEQ ID NO 56
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Arg
                 85                  90                  95

Thr Phe Gly Gln Gly Thr Lys Val Glu Ile Lys
            100                 105
```

<210> SEQ ID NO 57
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 57

```
Asp Ile Val Met Thr Gln Ser Gln Lys Phe Met Ser Thr Ser Val Gly
  1               5                  10                  15

Asp Arg Val Ser Ile Thr Cys Lys Ala Ser Gln Asn Val Arg Thr Ser
                 20                  25                  30

Val Ala Trp Tyr Gln Gln Lys Pro Gly Gln Ser Pro Lys Ala Leu Ile
             35                  40                  45

Tyr Leu Ala Ser Asn Arg His Thr Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Leu Gln His Trp Thr Tyr Pro Tyr
                 85                  90                  95

Thr Phe Gly Gly Gly Thr Lys Leu Glu Ile Lys
            100                 105
```

<210> SEQ ID NO 58
<211> LENGTH: 113
<212> TYPE: PRT
<213> ORGANISM: Artificial Sequence
<220> FEATURE:
<223> OTHER INFORMATION: Synthetic Polypeptide

<400> SEQUENCE: 58

```
Gly Ala Ser Gln Ser Val Leu Thr Gln Pro Val Ser Val Ser Gly Ser
  1               5                  10                  15

Pro Gly Gln Ser Ile Thr Ile Ser Cys Thr Gly Thr Ser Ser Asn Ala
                 20                  25                  30

Asp Thr Tyr Asn Leu Val Ser Trp Tyr Gln Gln Arg Pro Gly Lys Ala
             35                  40                  45

Pro Lys Leu Met Ile Tyr Glu Gly Thr Lys Arg Pro Ser Gly Val Ser
 50                  55                  60

Asn Arg Phe Ser Ala Ser Lys Ser Ala Thr Ala Ala Ser Leu Thr Ile
 65                  70                  75                  80

Ser Gly Leu Gln Pro Glu Asp Glu Ala Asp Tyr Tyr Cys Cys Ser Tyr
                 85                  90                  95

Ala Thr Ser Arg Thr Leu Val Phe Gly Gly Gly Thr Lys Leu Thr Val
            100                 105                 110

Val
```

<210> SEQ ID NO 59
<211> LENGTH: 115
<212> TYPE: PRT
<213> ORGANISM: Artificial Sequence
<220> FEATURE:
<223> OTHER INFORMATION: Synthetic Polypeptide

<400> SEQUENCE: 59

Gly Ala Ser Gln Ser Val Leu Thr Gln Pro Val Ser Val Ser Gly Ser
1               5                   10                  15

Pro Gly Gln Ser Ile Thr Ile Ser Cys Thr Gly Thr Ser Ser Asn Ala
            20                  25                  30

Asp Thr Tyr Asn Leu Val Ser Trp Tyr Gln Gln Arg Pro Gly Lys Ala
        35                  40                  45

Pro Lys Leu Met Ile Tyr Glu Gly Thr Lys Arg Pro Ser Gly Val Ser
    50                  55                  60

Asn Arg Phe Ser Ala Ser Lys Ser Ala Thr Ala Ala Ser Leu Thr Ile
65                  70                  75                  80

Ser Gly Leu Gln Pro Glu Asp Glu Ala Asp Tyr Tyr Cys Cys Ser Tyr
                85                  90                  95

Ala Thr Ser Arg Thr Leu Val Phe Gly Gly Gly Thr Lys Leu Thr Val
            100                 105                 110

Val Ala Ala
        115

<210> SEQ ID NO 60
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 60

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Ile Trp Ile Tyr
        35                  40                  45

Glu Ser Ser Lys Leu Ala Ser Gly Val Pro Val Arg Phe Ser Gly Ser
    50                  55                  60

Gly Ser Gly Thr Ser Tyr Ser Leu Thr Ile Ser Ser Met Glu Ala Glu
65                  70                  75                  80

Asp Val Ala Thr Tyr Tyr Cys Gln Gln Trp Ser Ser His Pro His Pro
                85                  90                  95

Leu Thr Phe Gly Ala Gly Thr Lys Leu Glu Leu Lys
            100                 105

<210> SEQ ID NO 61
<211> LENGTH: 115
<212> TYPE: PRT
<213> ORGANISM: Artificial Sequence
<220> FEATURE:
<223> OTHER INFORMATION: Synthetic Polypeptide

<400> SEQUENCE: 61

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Val Gly Ser Asn
            20                  25                  30

Tyr Val Tyr Trp Tyr Gln Gln Leu Pro Gly Thr Ala Pro Lys Leu Leu
        35                  40                  45

```
Ile Tyr Arg Asn Asn Arg Arg Pro Ser Gly Val Pro Asp Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Ala Thr Trp Asp Asp Ser Leu
                85                  90                  95
Ser Gly Leu Val Phe Gly Gly Thr Lys Leu Thr Val Leu Gly Gln
            100                 105                 110
Pro Lys Ala
        115
```

<210> SEQ ID NO 62
<211> LENGTH: 115
<212> TYPE: PRT
<213> ORGANISM: Artificial Sequence
<220> FEATURE:
<223> OTHER INFORMATION: Synthetic Polypeptide

<400> SEQUENCE: 62

```
Arg Ser Gln Ser Ala Leu Thr Gln Pro Ala Ser Val Ser Gly Ser Pro
1               5                   10                  15
Gly Gln Ser Ile Thr Ile Ser Cys Thr Gly Ile Ser Ser Asp Val Glu
            20                  25                  30
Thr Tyr Asn Leu Val Ser Trp Tyr Glu Gln His Pro Gly Lys Ala Pro
        35                  40                  45
Lys Leu Ile Ile Tyr Glu Ala Ser Lys Arg Pro Ser Gly Val Ser Asn
    50                  55                  60
Arg Phe Ser Gly Ser Lys Ser Gly Asn Thr Ala Ser Leu Ala Ile Ser
65                  70                  75                  80
Gly Leu Gln Ala Glu Asp Glu Ala Asp Tyr Tyr Cys Cys Ser Tyr Ala
                85                  90                  95
Gly Gly Lys Ser Leu Val Phe Gly Gly Gly Thr Arg Leu Thr Val Leu
            100                 105                 110
Gly Gln Pro
        115
```

<210> SEQ ID NO 63
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 63

```
Asp Ile Lys Met Thr Gln Ser Pro Ser Ser Met Tyr Ala Ser Leu Gly
1               5                   10                  15
Glu Arg Val Thr Ile Thr Cys Lys Ala Ser Gln Gly Ile Asn Ser Asp
            20                  25                  30
Leu Ser Trp Phe Gln Gln Lys Pro Gly Lys Ser Pro Lys Thr Leu Ile
        35                  40                  45
Tyr Arg Ala Asn Arg Leu Val Asp Gly Val Pro Ser Arg Phe Ser Gly
    50                  55                  60
Ser Gly Ser Gly Gln Asp Tyr Ser Leu Thr Ile Ser Ser Leu Glu Tyr
65                  70                  75                  80
Glu Asp Met Gly Ile Tyr Tyr Cys Leu Gln Tyr Asp Glu Phe Pro Leu
                85                  90                  95
Thr Phe Gly Ala Gly Thr Lys Leu Glu Leu Lys
            100                 105
```

<210> SEQ ID NO 64
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 64

```
Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Thr Pro Tyr
                85                  90                  95

Thr Phe Gly Gly Gly Thr Lys Leu Glu Ile Lys
            100                 105
```

<210> SEQ ID NO 65
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 65

```
Asp Ile Val Met Thr Gln Ser Pro Ala Ser Leu Ala Val Ser Leu Gly
1               5                   10                  15

Gln Arg Ala Thr Ile Ser Cys Arg Ala Ser Glu Asn Val Asp Lys Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Glu Leu Gln Trp Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Arg Ser Asn
                85                  90                  95

Glu Val Pro Trp Thr Phe Gly Gln Gly Thr Lys Leu Glu Ile Lys Arg
            100                 105                 110

Thr Val Ala His His His His His His
        115                 120
```

<210> SEQ ID NO 66
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 66

```
Ser Glu Ile Val Leu Thr Gln Ser Pro Ala Thr Leu Ser Leu Ser Pro
1               5                   10                  15
```

```
Gly Glu Arg Ala Thr Leu Ser Cys Arg Ala Ser Gln Ser Ile Ser Thr
            20                  25                  30

Phe Leu Ala Trp Tyr Gln His Lys Pro Gly Gln Ala Pro Arg Leu Leu
        35                  40                  45

Ile Tyr Asp Ala Ser Thr Arg Ala Thr Gly Val Pro Ala Arg Phe Ser
 50                  55                  60

Gly Ser Arg Ser Gly Thr Asp Phe Thr Leu Thr Ile Ser Thr Leu Glu
 65                  70                  75                  80

Pro Glu Asp Phe Ala Val Tyr Tyr Cys Gln Gln Arg Tyr Asn Trp Pro
                 85                  90                  95

Pro Tyr Thr Phe Gly Gln Gly Thr Lys Val Glu Ile Lys
            100                 105
```

<210> SEQ ID NO 67
<211> LENGTH: 113
<212> TYPE: PRT
<213> ORGANISM: Artificial Sequence
<220> FEATURE:
<223> OTHER INFORMATION: Synthetic Polypeptide

<400> SEQUENCE: 67

```
Gln Ser Val Leu Thr Gln Pro Val Ser Val Ser Gly Ser Pro Gly Gln
 1               5                  10                  15

Ser Ile Thr Ile Ser Cys Thr Gly Thr Ser Ser Asn Ala Asp Thr Tyr
            20                  25                  30

Asn Leu Val Ser Trp Tyr Gln Gln Arg Pro Gly Lys Ala Pro Lys Leu
        35                  40                  45

Met Ile Tyr Glu Gly Thr Lys Arg Pro Ser Gly Val Ser Asn Arg Phe
 50                  55                  60

Ser Ala Ser Lys Ser Ala Thr Ala Ala Ser Leu Thr Ile Ser Gly Leu
 65                  70                  75                  80

Gln Pro Glu Asp Glu Ala Asp Tyr Tyr Cys Cys Ser Tyr Ala Thr Ser
                 85                  90                  95

Arg Thr Leu Val Phe Gly Gly Gly Thr Lys Leu Thr Val Val Gly Gln
            100                 105                 110

Pro
```

<210> SEQ ID NO 68
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 68

```
Asn Ile Val Met Thr Gln Ser Pro Lys Ser Met Ser Met Ser Val Gly
 1               5                  10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
 50                  55                  60

Ser Gly Ser Ala Thr Asp Phe Thr Leu Thr Ile Ser Ser Val Gln Ala
 65                  70                  75                  80

Glu Asp Leu Ala Asp Tyr His Cys Gly Gln Gly Tyr Ser Tyr Pro Tyr
                 85                  90                  95
```

```
Thr Phe Gly Gly Gly Thr Lys Leu Glu Ile Lys
            100                 105
```

<210> SEQ ID NO 69
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 69

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105
```

<210> SEQ ID NO 70
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 70

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110
```

<210> SEQ ID NO 71
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 71

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asp
```

```
                20                  25                  30
Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asn Tyr Tyr Cys Ala Thr Trp Asp Arg Arg Pro
                85                  90                  95

Thr Ala Tyr Val Val Phe Gly Gly Gly Thr Lys Leu Thr Val Leu
            100                 105                 110
```

<210> SEQ ID NO 72
<211> LENGTH: 110
<212> TYPE: PRT
<213> ORGANISM: Artificial Sequence
<220> FEATURE:
<223> OTHER INFORMATION: Synthetic Polypeptide

<400> SEQUENCE: 72

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110
```

<210> SEQ ID NO 73
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 73

```
Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105
```